US009011933B2

(12) United States Patent
Sredni et al.

(10) Patent No.: US 9,011,933 B2
(45) Date of Patent: Apr. 21, 2015

(54) THERAPEUTIC METHODS AND PHARMACEUTICAL COMPOSITIONS FOR TREATING WARTS WITH TELLURIUM COMPOUNDS

(75) Inventors: Benjamin Sredni, Kfar-Saba (IL); Michael Albeck, Ramat-Gan (IL)

(73) Assignee: Biomas Ltd., Tel-Aviv (IL)

( * ) Notice: Subject to any disclaimer, the term of this patent is extended or adjusted under 35 U.S.C. 154(b) by 2492 days.

(21) Appl. No.: 10/586,746

(22) PCT Filed: Jan. 23, 2005

(86) PCT No.: PCT/IL2005/000084
§ 371 (c)(1),
(2), (4) Date: Sep. 2, 2010

(87) PCT Pub. No.: WO2005/069735
PCT Pub. Date: Aug. 4, 2005

(65) Prior Publication Data
US 2010/0330201 A1 Dec. 30, 2010

Related U.S. Application Data

(60) Provisional application No. 60/538,635, filed on Jan. 22, 2004.

(51) Int. Cl.
*A61K 31/555* (2006.01)
*A61K 33/24* (2006.01)
*A61K 38/22* (2006.01)
*A61P 17/10* (2006.01)
*A61P 25/24* (2006.01)
*A61P 31/12* (2006.01)
*A61K 9/00* (2006.01)
*A61K 31/095* (2006.01)
*A61K 33/04* (2006.01)
*A61K 47/06* (2006.01)
*A61K 47/20* (2006.01)

(52) U.S. Cl.
CPC ............ *A61K 9/0014* (2013.01); *A61K 31/095* (2013.01); *A61K 33/04* (2013.01); *A61K 47/06* (2013.01); *A61K 47/20* (2013.01)

(58) Field of Classification Search
None
See application file for complete search history.

(56) References Cited

U.S. PATENT DOCUMENTS

| | | |
|---|---|---|
| 4,752,614 A | 6/1988 | Albeck et al. |
| 4,761,490 A | 8/1988 | Albeck et al. |
| 4,764,461 A | 8/1988 | Albeck et al. |
| 4,929,739 A | 5/1990 | Sredni et al. |
| 4,962,207 A | 10/1990 | Albeck et al. |
| 5,093,135 A | 3/1992 | Albeck et al. |
| 5,102,908 A | 4/1992 | Albeck et al. |
| 5,213,899 A | 5/1993 | Lucas |
| 6,472,381 B1 * | 10/2002 | Albeck et al. ............... 514/162 |
| 2010/0055055 A1 * | 3/2010 | Albeck et al. ............... 424/59 |

FOREIGN PATENT DOCUMENTS

WO WO 2005/069735 8/2005

OTHER PUBLICATIONS

Jawaher Shah, National Journal of Homeopathy, Mar./Apr. 1994 vol. III No. 2.*
Kumar et al: Chemotherapy in Recurrent and Advanced Cervical Cancer, Gynecologic Oncology 40, 1991, pp. 107-111.
Examination Report Dated Feb. 19, 2009 From the Intellectual Property Office of New Zealand Re.: Application No. 548988.
International Preliminary Report on Patentability Dated Apr. 2, 2009 From the International Bureau of WIPO Re.: Application No. PCT/IL2005/000084.
International Search Report and the Written Opinion Dated Jul. 3, 2008 From the International Searching Authority Re.: Application No. PCT/IL05/00084.
Lima et al. "A Novel Organotellurium Compound (RT-01) as a New Antileishmanial Agent", Korean Journal of Parasitology, 47(3): 213-218, Sep. 2009.
Persike et al. "Protective Effect of the Organotelluroxetane RF-07 in Pilocarpine-Induced Status Epilepticus", Neurobiology of Disease, 31: 120-126, 2008.
Friedman et al., "Topical treatment for human papillomavirus-associated genital warts in humans with the novel tellurium immunomodulator AS101: assessment of its safety and efficiacy," Br. J. Derm 160:403-408 (2009), epub 2008.
U.S. Appl. No. 60/610,660, filed Sep. 17, 2004.
Belisario et al., "Warts and Their Treatment" Australas J Dermatol, 1951; 1:20-30 (1950).
Bennett and Reich., Diagnosis and Treatment, Drugs Five Years Later, Bleomycin Ann Intern Med, 1979; 90:945-948 (1979).
Berth-Jones et al., "Modern treatment of warts: cure rates at 3 and 6 months" Br J Dermatol, 127(3):262-5 (1992).
Beutner et al., Therapeutics, Patient-Applied Podofilox for Treatment of Genital Warts, Lancet, 1831-834 (1989).
Erkens et al., "Het einde van het wrattenspreekuur? Een gerandomiseerd onderzoek naar de effectiviteit van vloeibare stikstof en van de Histofreezer"J. A., Ned Tijdschr Geneeskd, 1991; 135(5):171-4.

(Continued)

*Primary Examiner* — Mina Haghighatian
(74) *Attorney, Agent, or Firm* — Browdy and Neimark, PLLC

(57) ABSTRACT

A novel method for treating skin and mucosal membrane ailments caused by human papilloma viruses, which utilizes tellurium-containing compounds, is disclosed. Also disclosed are pharmaceutical compositions containing tellurium-containing compounds for treating such ailments.

13 Claims, 18 Drawing Sheets
(18 of 18 Drawing Sheet(s) Filed in Color)

(56) References Cited

OTHER PUBLICATIONS

Ewin, D. M., "Hypnotherapy for Warts (Verruca Vulgaris): 41 Consecutive Cases With 33 Cures" Am J Clin Hypn, 35 (1):1-10 (1992).
Goldfarb et al., "Office Therapy for Human Papillomavirus Infection in Nongenital Sites" Dermatol Clin, 9(2):287-96 (1991).
Hayes and O'Keefe., "Reduced dose of bleomycin in the treatment of recalcitrant warts" J Am Acad Dermatol, 15:1002-1006 (1986).
Hettich., "Solcoderm as a Tool for the Plastic Surgeon, The Treatment of Verrucae" Dermatologica, 168 Supple 1:36-42 (1984).
Keefe and Dick."Cryotherapy of hand warts—a questionnaire survey of 'consumers'" Clin Exp Dermatol, 15(4):260-3 (1990).
Mishima and Matunaka., "Effect of Bleomycin on Benign and Malignant Cutaneous Tumours" Acta Derm Venereol (Stockh), 52:211-215 (1972).
Shelley and Shelley., "Intralesional Bleomycin Sulfate Therapy for Warts" Arch Dermatol, 127(2):234-6 (1992).
Sobh et al., "tntralesional Injection of Bleomycin Sulphate into Resistant Warts in Renal Transplant Recipients versus Non-transplant Warty Patients" Acta Derm Venereol Stockh, 71(1):63-6 (1991).
Robson et al., "Pulsed-dye laser versus conventional therapy in the treatment of warts: A prospective randomized trial" J Am Acad Dermatol, 43(2 Pt 1):275-80 (2000).
Sredni et al., "A new immunomodulating compound (AS-101) with potential therapeutic application". vol. 330, No. 6144, pp. 173-176 (1987).
Rosenblatt-Bin et al.,"Antibabesial effect of the immunomodulator AS101 in mice: role of increased production of nitric oxide". Parasite Immunol, 18:297-306 (1996).
Kalechman et al., "Delay in the onset of systemic lupus erythematosus following treatment with the immunomodulator AS101: association with IL-10 inhibition and increase in TNF-alpha levels". J Immunol, pp. 2658-2667 (1997).
Kalechman et al., "Effect of the immunomodulator AS101 on chemotherapy-induced multilineage myelosuppression, thrombocytopenia, and anemia in mice". Experimental Hematology 23:1358-1366(1995).
Kozenitzky et al., "Immunomodulatory effects of AS101 on interleukin-2 production and T-lymphocyte function of lymphocytes treated with psoralens and ultraviolet A". Photodermatol Photoimmunol Photomed (1992).
Vonsover et al.,"Inhibition of the reverse transcriptase activity and replication of human immunodeficiency virus type 1 by AS101 in vitro". AIDS Research and Human Retroviruses, vol. 8, No. 5 (1992).
Kalechman et al.,"Mechanism of radioprotection conferred by the immunomodulator AS101". Exp Hematol 21:150-155 (1993).
Sredni et al.,"Predominance of TH1 response in tumor-bearing mice and cancer patients treated with AS101". Journal of the National Cancer Institute, vol. 88, No. 18, (1996).
Montero et al., "AS-101: a modulator of in vitro T-cell proliferation". Anticancer Drugs, 4, pp. 351-354 (1993).
Sredni et al.,"Restoration of murine cytomegalovirus (MCMV) induced myelosuppression by AS101". Immunol Lett 43:159-165 (1994).
Kalechman et al.,"The antitumoral effect of the immunomodulator AS101 and paclitaxel (Taxol) in a murine model of lung adenocarcinoma" The Journal of Immunology, 156: 1101-1109 (1996).
Sredni et al.,"The biological activity and immunotherapeutic properties of AS-101, a synthetic organotellurium compound". Nat Immun Cell Growth Regul 7:163-168 (1988).
Blank et al., "The effect of the immunomodulator agent AS101 on interleukin-2 production in systemic lupus erythematosus (SLE) induced in mice by a pathogenic anti-DNA antibody". Clin. exp. Immunol. 79, 443-447 (1990).
Sredni et al.,"The immunomodulator AS101 administered orally as a chemoprotective and radioprotective agent". Int J Immunopharmacol, 14(4):613-619 (1992).
Strassmann et al.,"The immunomodulator AS-101 inhibits IL-10 release and augments TNF alpha and IL-1 alpha release by mouse and human mononuclear phagocytes". Cell Immunol Cellular Immunology 176, 180-185 (1997).
Rosenblatt-Bin et al.,"The immunomodulator AS101 restores T(H1) type of response suppressed by *Babesia rodhaini* in BALB/c mice". Cell Immunol Cellular Immunology 184, 12-25 (1998).
Sredni et al.,"The protective role of the immunomodulator AS101 against chemotherapy-induced alopecia studies on human and animal models". Int. J. Cancer: 65:97-103 (1996).
Nyska et al.,"Toxicity study in rats of a tellurium based immunomodulatory drug, AS-101: a potential drug for AIDS and cancer patients". Arch Toxicol 63:386-393 (1989).
Kalechman et al.,"Up-regulation by ammonium trichloro(dioxoethylene-0,0') tellurate (AS101) of Fas/Apo-1 expression on B16 melanoma cells: implications for the antitumor effects of AS101". The Journal of Immunology, 161: 3536-3542 (1998).
Kalechman et al.,"Use and mechanism of action of AS101 in protecting bone marrow colony forming units-granulocyte-macrophage following purging with ASTA-Z 7557" Cancer Research 51:5614-5620 (1991).
Kimmerle et al., Vergleichende Untersuchungen der Inhalationstoxicitat von Schwefel-, Selenund Tellurhexafluorid Arch. Toxikol. 18: 140-144 (1960) (In German).
Vonsover et al., "Inhibition of the Reverse Transcriptase Activity and Replication of Human Immunodeficiency Virus Type 1 by AS 101 In Vitro," AIDS Research and Human Retroviruses, 8:613-623 (1992).
Albeck et al., "Tellurium Compounds: Selective Inhibition of Cysteine Proteases and Model Reaction with Thiols," Inorg. Chem. 37:1704-1712 (1998).
Frei et al., "Neutral and positively charged thiols synergize the effect of the immunomodulator AS101 as a growth inhibitor of Jurkat cells, by increasing its uptake," Biochem Pharmacol, 74:712-722 (2007).

\* cited by examiner

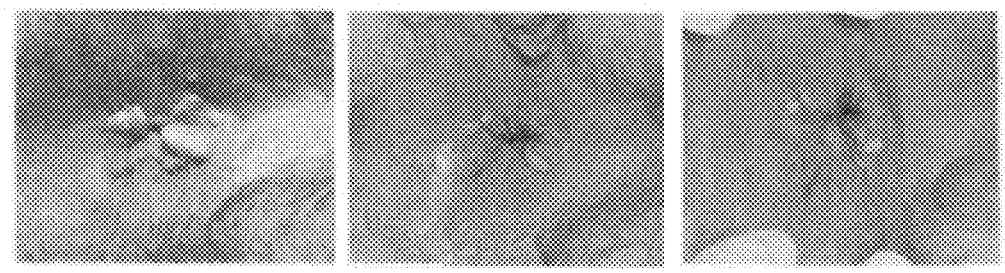
FIG. 1   FIG. 2   FIG. 3
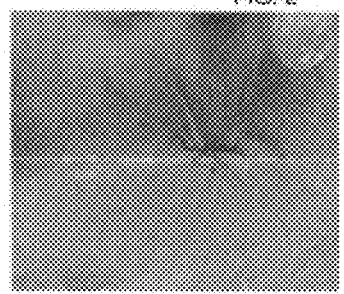 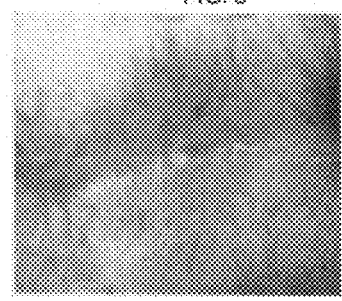
FIG. 4   FIG. 5

THERAPEUTIC METHODS AND PHARMACEUTICAL COMPOSITIONS FOR TREATING WARTS WITH TELLURIUM COMPOUNDS

RELATED APPLICATIONS

This application is a National Phase Application of PCT Patent Application No. PCT/IL2005/000084 having International Filing Date of Jan. 23, 2005, which claims the benefit of U.S. Provisional Patent Application No. 60/538,635 filed on Jan. 22, 2004. The contents of the above Applications are all incorporated herein by reference.

FIELD AND BACKGROUND OF THE INVENTION

The present invention relates to novel therapeutic methods and pharmaceutical compositions for treating warts. More particularly, the present invention relates to novel therapeutic methods and pharmaceutical compositions for treating ailments caused by human papilloma viruses.

Human papilloma virus (HPV) infections are common infections of the outer layer of the skin, which affect most persons sometime during their lifetime. To date, over seventy distinct types of HPVs have been already identified. These viruses target the squamous epithelia of the skin and mucosal membranes. Based on this trophism, the different types of HPV have been subdivided into two large categories: cutaneous and mucosal. A third category is sometimes used to designate types of HPV specifically found in people with epidermodysplasia verruciformis (EV).

HPV infections typically emerge as skin warts. However, by being spread by auto-innoculation, warts may also occur at any other location in the body. Subjects afflicted with warts may in some cases experience complete regression after several months with or without treatment with recurrence at the same or at different locations.

Skin warts include, for example, common warts (e.g., verruca vulgaris, plantar, palmar and periungal); planar warts (verruca plana); mosaic warts; genital and venereal warts (e.g., condylomata acuminata); butcher's warts; malignant epidermodyspasia verruciformis; advanced intraepithelial dysplasia, mepidermodysplasia verruciformis; cutnaeous warts in immunosuppressed patients; laryngeal papillomas; and oral papilloma. However, clinical manifestations sometimes further include serious infections of the genital mucous membranes, (e.g., advanced intraepithelial dysplasia), which may progress to cervical cancer.

Skin warts resulting from HPVs are unsightly and irritating, and although the majority of such infections are benign and self-limited, there are subtypes of papilloma virus that are considered pre-malignant in certain clinical settings. Therefore, the removal of emerged skin warts is highly recommended.

Throughout the years a number of therapies have been developed for treating these coetaneous infections. However, most of the presently known methods of treating warts are painful, expensive, requiring long treatment periods and/or are ineffective. Most of these methods are initially successful but involve a longer-term treatment failure, exhibited by recurrence, as well as side effects [see, for example, Goldfarb et al., Dermatol Clin, 1991; 9(2):287-96; Hettich, Dermatologica, 1984; 168 Supple 1:36-42; Bunney, M. H., Viral warts: their biology and treatment. New York, N.Y.: Oxford University Press Inc., 1982; Belisario, Australas J Dermatol, 1951; 1:20-30; and Beutner et al. Lancet, 1989; 1831-834].

The presently used methods of treating HPV infections typically include the use of locally destructive chemicals or agents, such as salicylic acid, lactic acid, trichloracetic acid, dichloroacetic acid, nitric acid and glacial acetic acid; surgically destructive methods such as excision, electrocautery, electrodesiccation, curettage, blunt dissection and laser vaporization or coagulation; blister-producing methods such as liquid nitrogen cryotherapy, carbon dioxide cryotherapy and cantharidin; cellular inhibition, which uses agents such as podophyllin and podophyllotoxin, 5-fluorouracil, bleomycin, colchicine, interferon local injections and radiation; altering the cutaneous environment, which includes agents or techniques such as retinoids, formalin, glutaraldehyde, aluminum chloride and heat therapy; and immune stimulation methods of treatment, which include dinitrochlorobenzene (DNCB), imiquimod (also known by the trade name Aldara™), interferon systemic injections and vaccination, either autologous or intralesional.

Hence, the presently most common methods of warts treatment can be divided into chemical, surgical and physical methods. The physical methods typically include destruction of the infected keratinocytes by cooling (e.g., liquid nitrogen) or heating (e.g., electrocautery, $CO_2$ laser), and often lead to injury of surrounding tissues, secondary infections and other undesired consequences.

Surgical treatments are typically associated with discomfort, prolonged healing and the formation of scars and/or keloids, is addition to an inherent risk.

The chemical methods commonly use locally destructive chemicals and typically include caustic chemicals that act through nonspecific destructive mechanisms to cause cell death, killing the infected keratinocytes. The keratinocytes are subsequently desquamated from the skin surface. This non-specific form of destructive therapy often causes side effects such as pain, secondary infection, permanent scarring and is oftentimes associated with recurrence of disease.

The chemical methods typically involve topical application of the chemical agents as solutions, tinctures, creams, ointments, patches, etc. One of the presently most used chemical agents for treating warts is salicylic acid, which is typically administered as a patch or a gel. A typical salicylic acid patch contains an amount of salicylic acid in a sticky base or a rubber base. However, the use of salicylic acid in the treatment of HPV requires repeated administration of the composition for a prolonged period of about 4-6 weeks, and is oftentimes unsuccessful.

Hence, most of the currently available methods focus on the destruction of visible lesions rather than the underlying cause of disease, namely the HPV. For example, removal of warts with destructive chemical agents or with physical ablative means do not affect viral particles that may be lurking in normal-appearing areas surrounding the wart. This is one of the reasons of the high rate of disease recurrence.

The inefficiency of the presently known methods of treating warts have been widely studied and reported in the art. Thus, it was found that using a liquid nitrogen, initial cure is seen in 52-83% of patients [Berth-Jones and Hutchinson, Br J Dermatol, 1992; 127(3):262-5; Erkens et al., J. A., Ned Tijdschr Geneeskd, 1991; 135(5):171-4]; Keefe and Dick. Clin Exp Dermatol, 1990; 15(4):260-3], however, only 57% of the patients remain clear of warts after a median of 19 months [Keefe and Dick. Clin Exp Dermatol, 1990; 15(4): 260-3].

When using a histofreezer technique the success rate falls to 28% [Erkens et al., J. A., Ned Tijdschr Geneeskd, 1991; 135(5):171-4] and is comparable with placebo or the success rates achieved through direct in hypnotic suggestion (27-

55%) [Ewin, D. M., Am J Clin Hypn, 1992; 35(1):1-10]. Recently, however, individual byproanalytic techniques were shown to cure 80% of patients who have failed hypnosis [Robson et al., J Am Acad Dermatol, 2000; 43(2 Pt 1):275-80].

Since 1970 intralesional bleomycine therapy success rate has remained in the 70% range [see, for example, Sobh et al., Acta Derm Venereol Stockh, 1991; 71(1):63-6; Shelley and Shelley, Arch Dermatol, 1991; 127(2):234-6; Hayes and O'Keefe, J Am Acad Dermatol, 1986; 15:1002-1006; Mishima and Matunaka, Acta Derm Venereol (Stockh), 1971; 52:211-215; and Bennett and Reich, Ann Intern Med, 1979; 90:945-948]. However, it was found that not all warts are suitable for intralesional bleomycine, the treatment exhibit significant systemic drug exposure and significant local adverse and side effects. In addition, multiple treatments are required to achieve substantial success.

Summarizing various published reports indicates that topical standard salicylic acid treatment results, at best, in 40% cure rate after 4 weeks compared to 8% cure in the placebo group. Treatment with trichloro acetic acid typically results in 64-81% cure rate, whereby treatment with 5-fluorouracil typically results in even lower cure rates ranging from 10 to 50%. Carbon dioxide laser evaporation for recalcitrant warts results in 31-86% cure rate. This treatment, however, may result in significant morbidity.

Using superpulsed mode to overcome these limitations was found to convey only a slight advantage. Comparable results were obtained with infrared coagulation. Early studies with pulsed dye lasers showed promising results, which have not been confirmed yet by later studies.

Since recalcitrant and recurrent warts are more common in patients with a cell-mediated immune deficiency state, it is suggested that spontaneous regression or successful treatment depend on either naturally or iatrogenically related stimulation of immunity [Robson et al. J Am Acad Dermatol, 2000; 43(2 Pt 1):275-80]. Thus, several systemic and topical immunotherapies for warts have been reported, including squalic acid dibutylester, levamizole, and interferons beta and gamma. The efficacy of these therapies, however, was not definite.

The presently known methods for treating warts therefore suffer major disadvantages, in terms of both efficacy and adverse side effects associated therewith.

There is thus a widely recognized need for, and it would be highly advantageous to have novel methods of treating warts, devoid of the above limitations.

Various tellurium compounds have been described in the art as having immunomodulating properties. These compounds are taught, for example, in U.S. Pat. Nos. 4,752,614; 4,761,490; 4,764,461 and 4,929,739, and in a recently filed U.S. Provisional Patent Application No. 60/610,660, which are all incorporated by reference as if fully set forth herein. U.S. Pat. No. 4,752,614, which is also incorporated by reference as if fully set forth herein, teaches the use of certain tellurium compounds in the treatment of certain tumors, autoimmune diseases, immune diseases and infectious diseases. An anti-viral activity of these compounds was demonstrated in this patent in plants and animals, whereby the virus that is exemplified is West Nile Virus, which affects the central nervous system.

The use of tellurium compounds to treat HPV and hence warts has never been suggested nor practiced hitherto.

SUMMARY OF THE INVENTION

According to one aspect of the present invention there is provided a method of treating a skin or mucosal membrane ailment caused by a human papilloma virus (HPV) in a subject in need thereof. The method comprises administering to the subject a therapeutically effective amount of at least one tellurium-containing compound.

According to further features in preferred embodiments of the invention described below, the tellurium-containing compound is selected from the group consisting of tellurium dioxide ($TeO_2$), a complex of $TeO_2$, a compound having general Formula I:

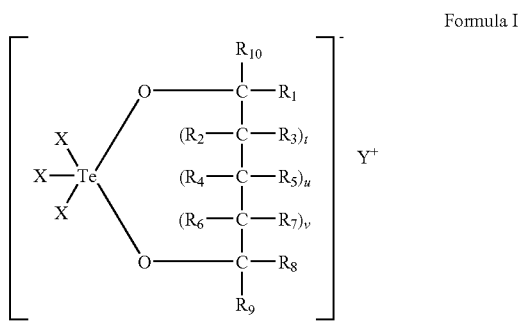

Formula I a compound having general Formula II:

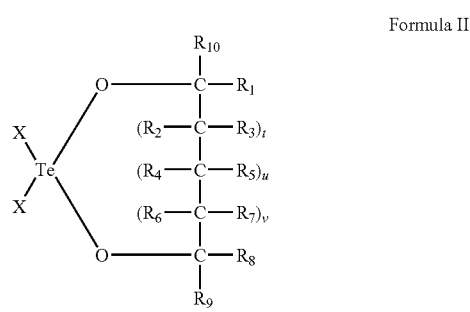

Formula II a compound having general Formula III:

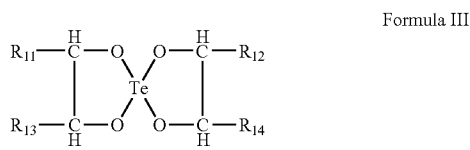

Formula III and a compound having general Formula IV:

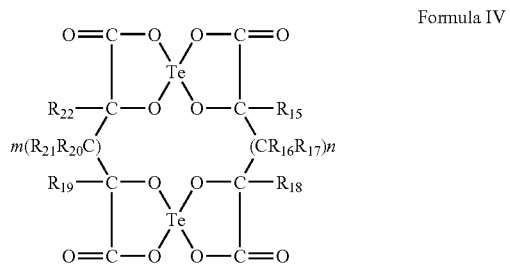

Formula IV wherein:
    each of t, u and v is independently 0 or 1;
    each of m and n is independently an integer from 0 to 3;
    X is a halogen atom;
    Y is selected from the group consisting of ammonium, phsophonium, potassium, sodium and lithium; and
    each of $R_1$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido.

Preferred tellurium-containing compounds are those having general Formula I above and those having general Formula II above.

More preferred compounds are those having one or more of the following features:
    t, u and v are each 0;
    each of $R_1$, $R_8$, $R_9$ and $R_{10}$ is hydrogen;
    X is a halogen atom, preferably chloro; and
    Y is ammonium or phosphonium, preferably ammonium.

Additional preferred compounds are those having general Formula III above, wherein, preferably, each of $R_{11}$-$R_{14}$ is hydrogen.

Additional preferred compounds are those having general Formula IV above.

More preferred compounds in this category are those having one or more of the following features:
    n and m are each 0; and
    each of $R_{15}$, $R_{18}$, $R_{19}$ and $R_{22}$ is hydrogen.

According to further features in preferred embodiments of the invention described below, the administering is effected systemically.

According to still further features in the described preferred embodiments the therapeutically effective amount ranges from about 0.01 mg/m$^2$/day to about 10.0 mg/m$^2$/day.

According to further features in preferred embodiments of the invention described below, the administering is effected topically.

According to still further features in the described preferred embodiments topically administering the compound is effected by applying onto a treated skin or mucosal membrane area a therapeutically effective amount of the at least one tellurium-containing compound described above.

According to still further features in the described preferred embodiments the skin or mucosal membrane ailment is selected from the group consisting of verruca vulgaris, plantar warts, palmar warts, periungal warts, planar warts, mosaic warts, genital warts, venereal warts (condylomata acuminata), butcher's warts, malignant epidermodyspasia verruciformis, advanced intraepithelial dysplasia, cervical cancer, mepidermodysplasia verruciformis, cutnaeous warts in immunosuppressed patients, laryngeal papillomas and oral papilloma.

According to still further features in the described preferred embodiments the method further comprises administering to the subject an additional active agent.

The additional active agent can be, for example, an antibiotic agent, an antimicrobial agent, an anti-acne agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, a chemotherapeutic agent, an antidepressant, an anti histamine, a vitamin, a hormone, a keratolytic agent and an antidandruff agent.

According to still further features in the described preferred embodiments the method further comprises administering to the subject an additional active agent that is capable of treating the skin or mucosal membrane ailment caused by the HPV.

According to still further features in the described preferred embodiments the tellurium-containing compound forms a part of a pharmaceutical composition, which further comprises a pharmaceutically acceptable carrier.

Hence, according to another aspect of the present invention there is provided a pharmaceutical composition identified for use in the treatment of a skin or mucosal membrane ailment caused by a human papilloma virus (HPV), comprising at least one tellurium-containing compound as described hereinabove and a pharmaceutically acceptable carrier.

According to further features in preferred embodiments of the invention described below, a concentration of the at least one tellurium-containing compound ranges from about 0.01 weight percent to about 50 weight percents of the total weight of the composition.

According to still further features in the described preferred embodiments the concentration of the at least one tellurium-containing compound ranges from about 5 weight percents to about 25 weight percents of the total weight of the composition.

According to still further features in the described preferred embodiments, when used for topical application, the pharmaceutical composition is being in a form selected from the group consisting of a cream, an ointment, a paste, a gel, a lotion, a milk, a suspension, a solution, an aerosol, a spray, a foam, a shampoo, a mousse, a serum, a swab, a pledget, a pad, a tincture, a patch and a soap.

According to still further features in the described preferred embodiments the pharmaceutical composition further comprises at least one additional active agent, as described hereinabove.

According to still further features in the described preferred embodiments the pharmaceutical composition further comprises at least one ingredient such as, but not limited to, a humectant, a deodorant agent, an antiperspirant, a sun screening agent, a sunless tanning agent, a hair conditioning agent, a pH adjusting agent, a chelating agent, a preservative, an emulsifier, an occlusive agent, an emollient, a thickener, a solubilizing agent, a penetration enhancer, an anti-irritant, a colorant, a propellant and a surfactant.

According to still further features in the described preferred embodiments the pharmaceutical composition has a pH that ranges from 4 to 7.

According to still further features in the described preferred embodiments the pharmaceutical composition has a pH that ranges from 4 to 6.

The present invention successfully addresses the shortcomings of the presently known configurations by providing novel compositions and methods utilizing same for treating warts and related ailments caused by HPVs, which are highly efficient, and induce minimal or no adverse side effects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "active ingredient" refers to a pharmaceutical agent including any natural or synthetic chemical substance that subsequent to its application has, at the very least, at least one desired pharmaceutical or therapeutic effect.

The term "therapeutically effective amount" or "pharmaceutically effective amount" denotes that dose of an active ingredient or a composition comprising the active ingredient that will provide the therapeutic effect for which the active ingredient is indicated, herein, treating an HPV-caused ailment.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a photograph of the perianal area of a patient afflicted with condyloma warts, as described in Example 2, before treatment;

FIG. 2 is a photograph of the perianal area of a patient afflicted with condyloma warts, as described in Example 2, following about two weeks of treatment with an exemplary composition according to the present invention;

FIG. 3 is a photograph of the perianal area of a patient afflicted with condyloma warts, as described in Example 2, following about four weeks of treatment with an exemplary composition according to the present invention;

FIG. 4 is a photograph of the perianal area of a patient afflicted with condyloma warts, as described in Example 2, following about six weeks of treatment with an exemplary composition according to the present invention;

FIG. 5 is a photograph of the perianal area of a patient afflicted with condyloma warts, as described in Example 2, following about eight weeks of treatment with an exemplary composition according to the present invention;

FIG. 6 is a photograph of a patient afflicted with verrucca lesion on the hand, as described in Example 3, before treatment;

FIG. 7 is a photograph of a patient afflicted with verrucca lesion on the hand, as described in Example 3, following about four weeks of treatment with an exemplary composition according to the present invention;

FIG. 8 is a photograph of a patient afflicted with verrucca lesion on the hand, as described in Example 3, following about ten weeks of treatment with an exemplary composition according to the present invention;

FIG. 9 is a photograph of a patient afflicted with verrucca lesions on the hand, as described in Example 4, before treatment;

FIG. 10 is a photograph of a patient afflicted with verrucca lesions on the hand, as described in Example 4, following about two weeks of treatment with an exemplary composition according to the present invention;

FIG. 11 is a photograph of a patient afflicted with verrucca lesions on the hand, as described in Example 4, following about four weeks of treatment with an exemplary composition according to the present invention;

Figure 12A:
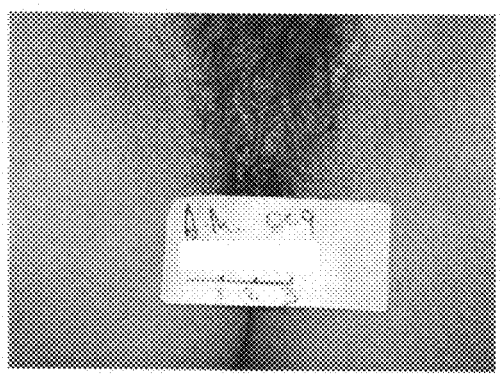
Figure 12B:
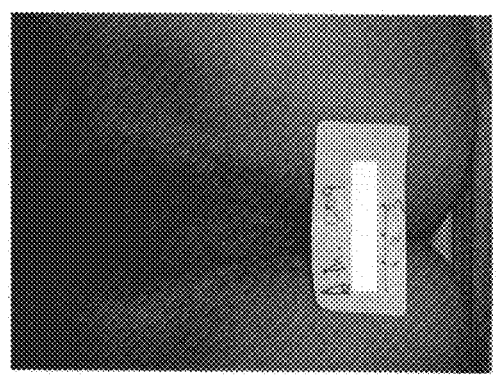
Figure 12C:
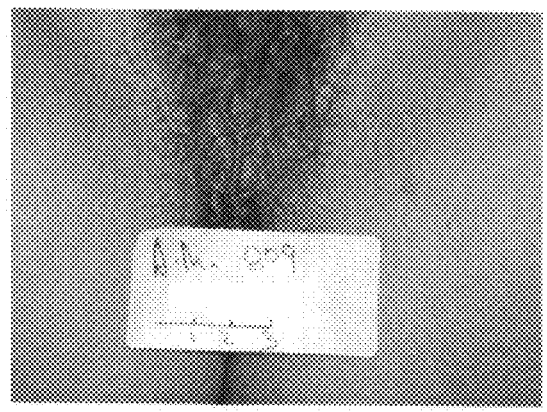
Figure 13A:
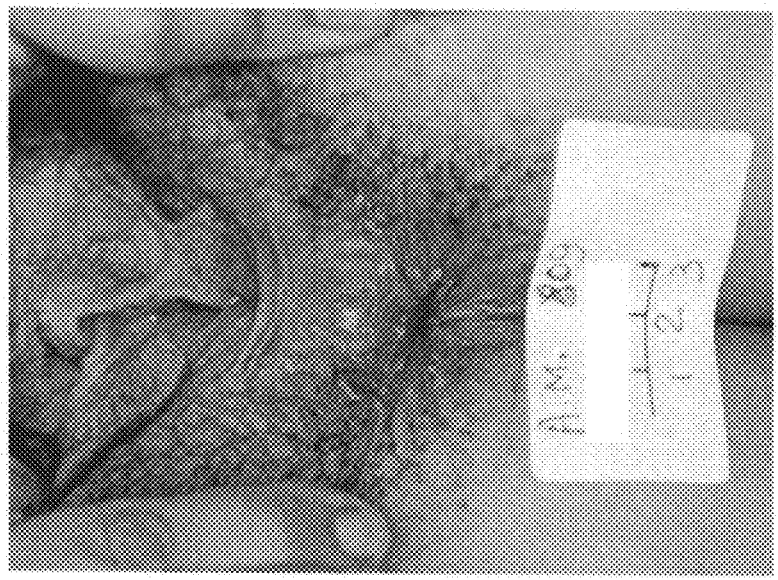
Figure 13B:
Figure 14A:
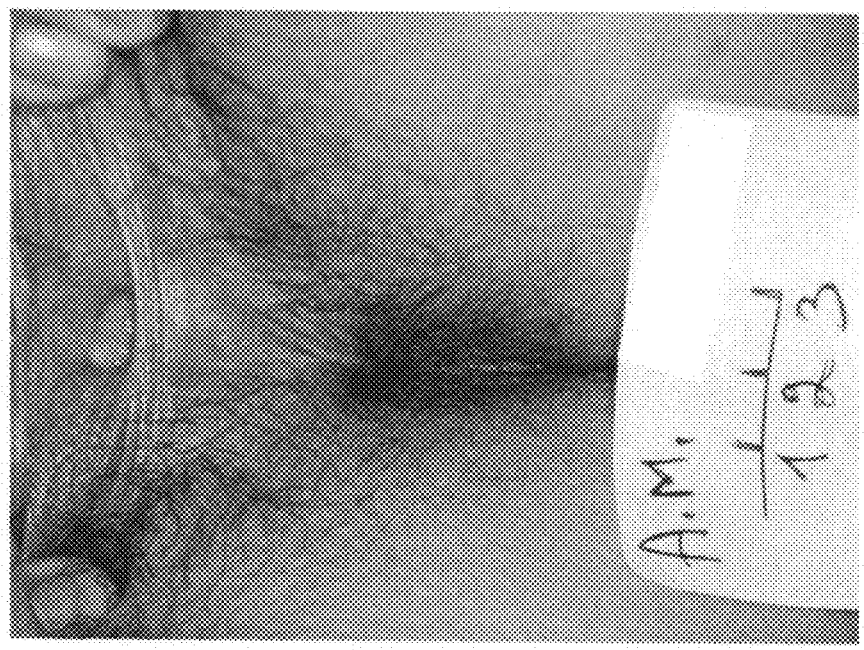
Figure 14B:
Figure 15A:
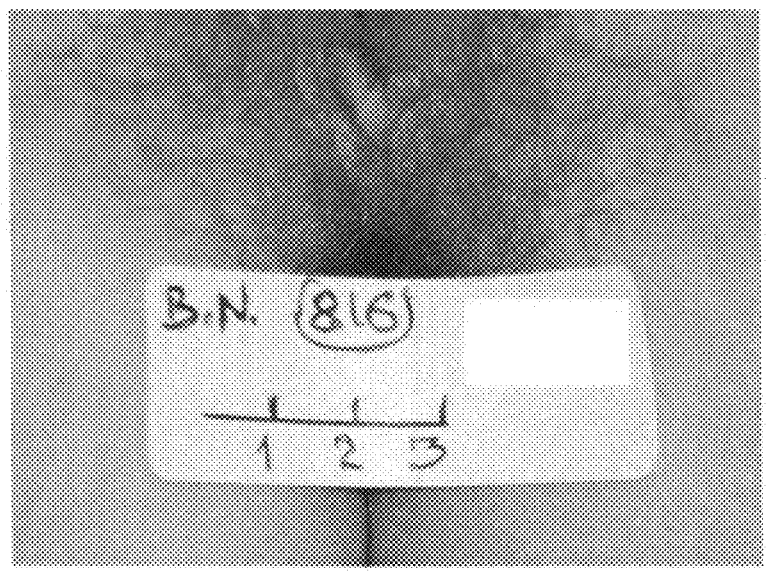
Figure 15B:
Figure 16A:
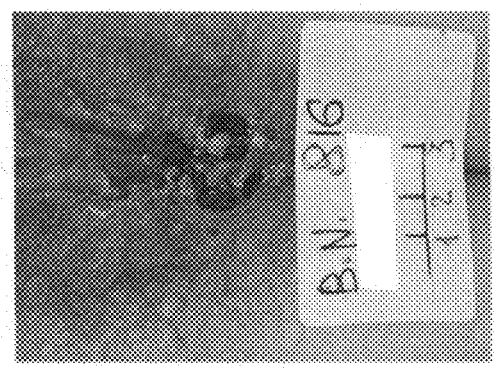
Figure 16B:
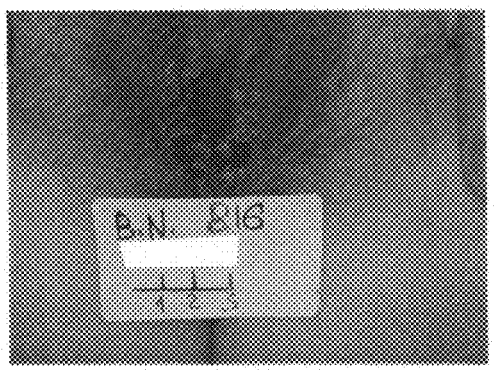
Figure 16C:
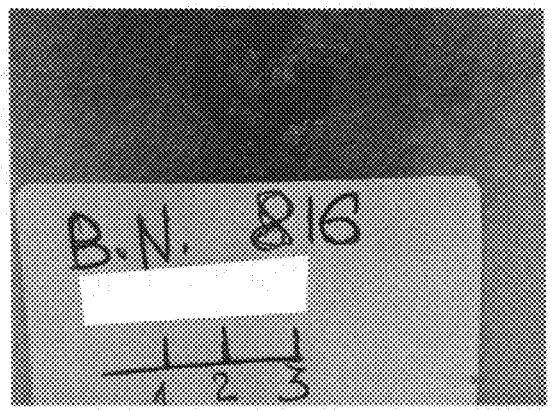
Figure 17:
Figure 18:
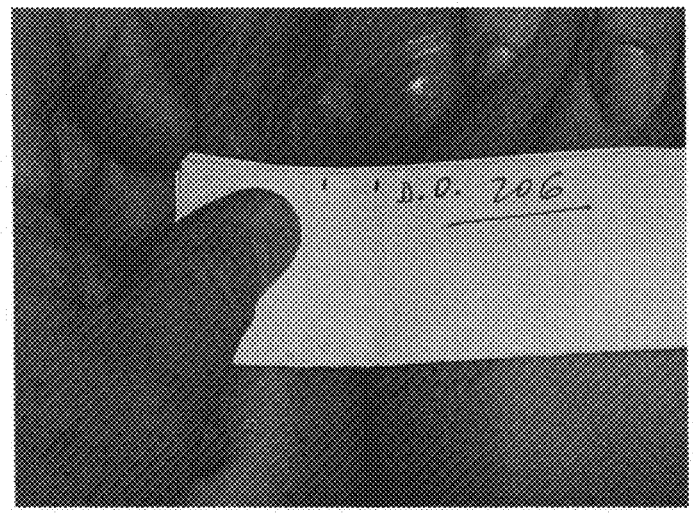
Figure 19:
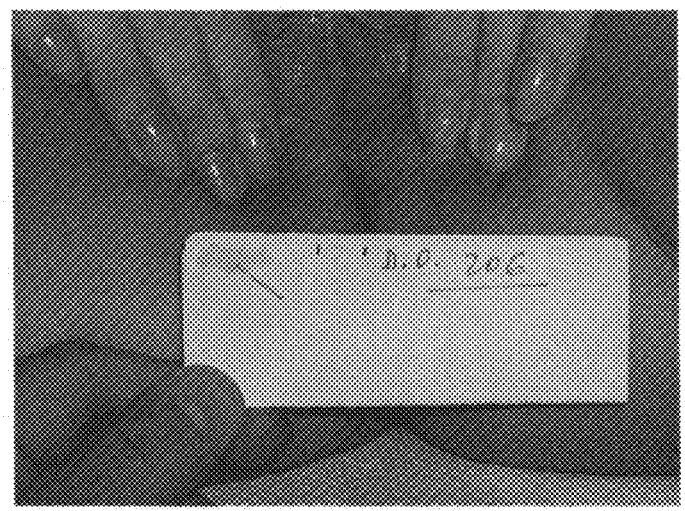
Figure 20:
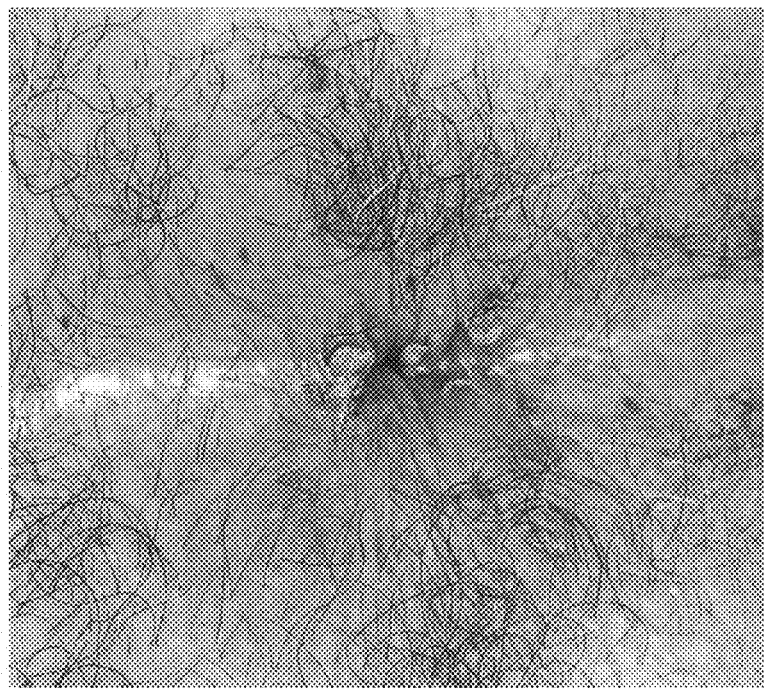
Figure 21:
Figure 22:
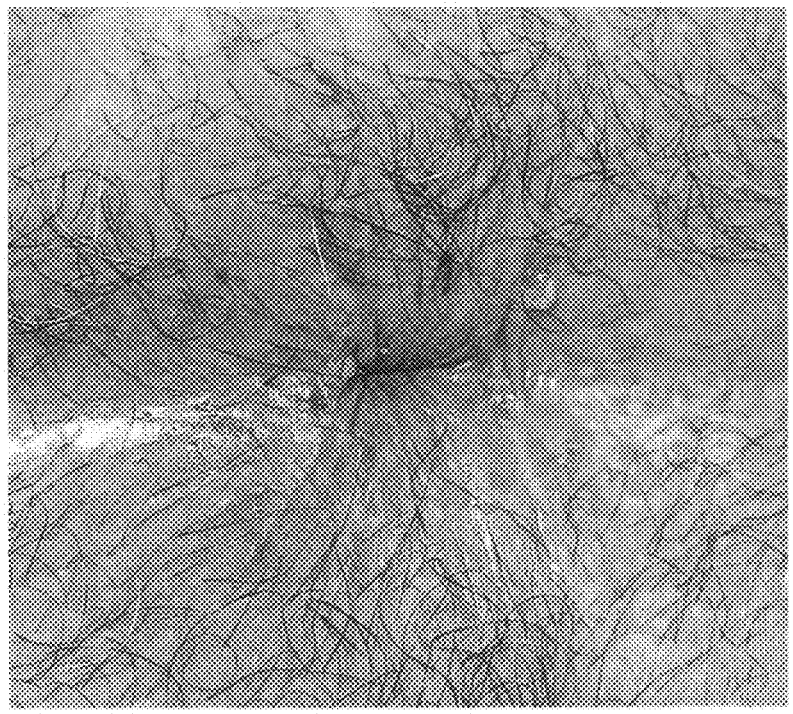
Figure 23:
Figure 24A:
Figure 24B:
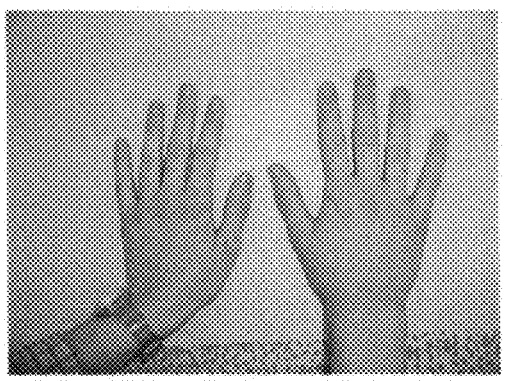
Figure 25A:
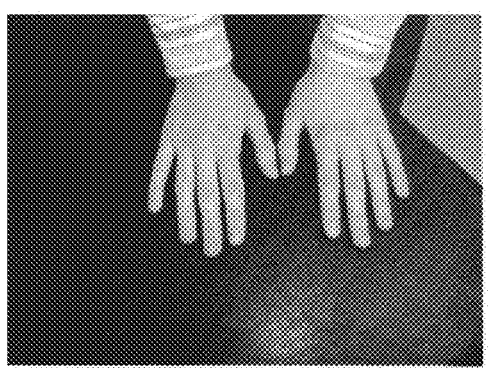
Figure 25B:
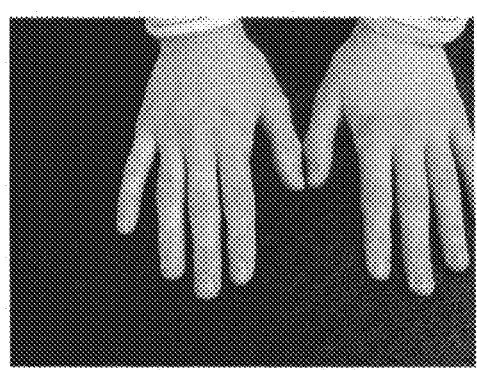
Figure 26A:
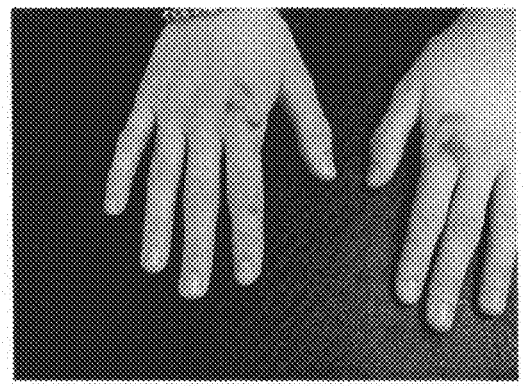
Figure 26B:
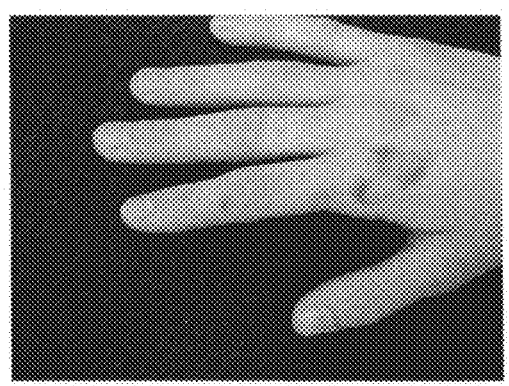
Figure 27A:
Figure 27B:
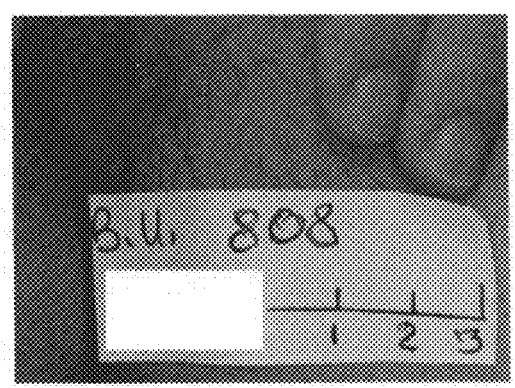
Figure 27C:
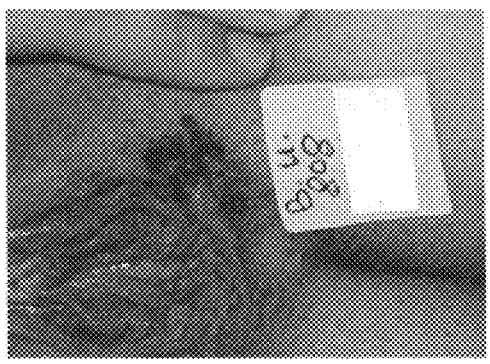
Figure 27D:
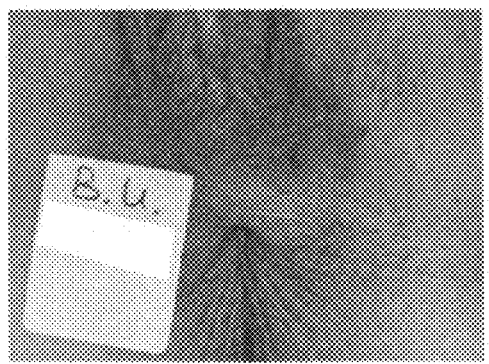
Figure 28A:
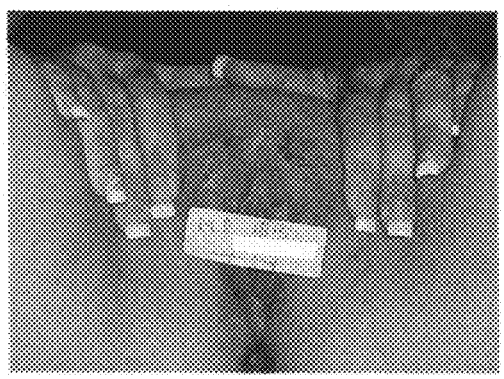
Figure 28B:
Figure 28C:
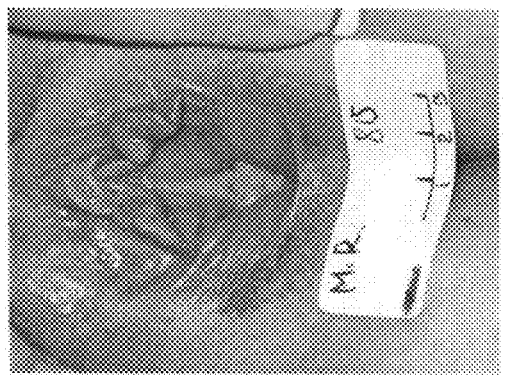
Figure 28D:
Figure 29A:
Figure 29B:
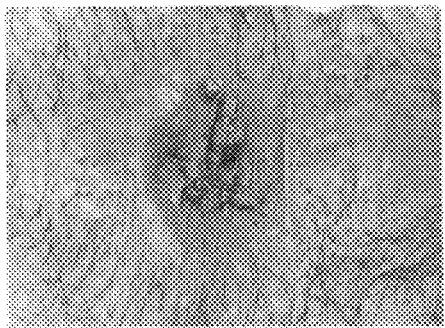
Figure 29C:
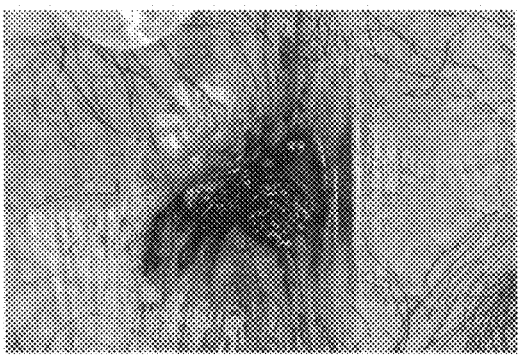
Figure 29D:
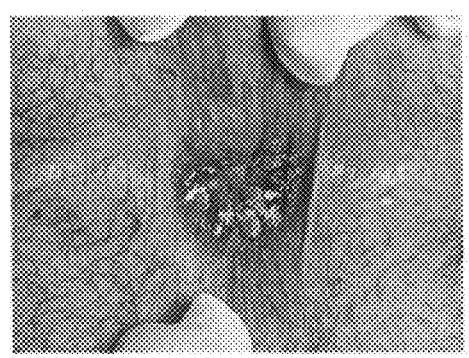
Figure 29E:
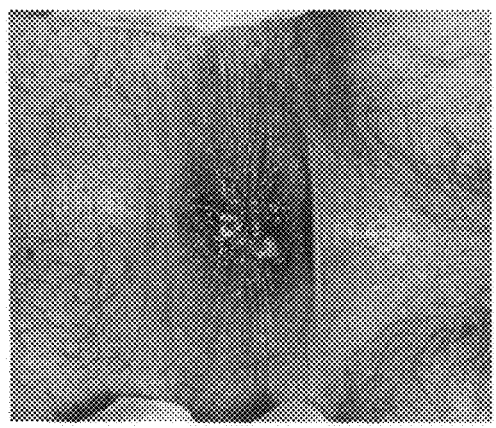
Figure 30A:
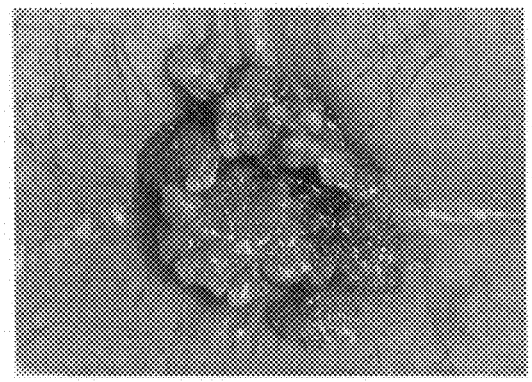
Figure 30B:
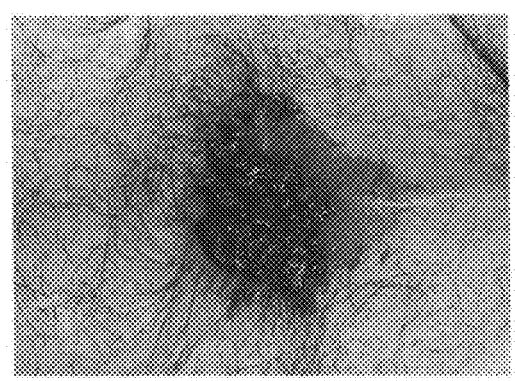
Figure 30C:
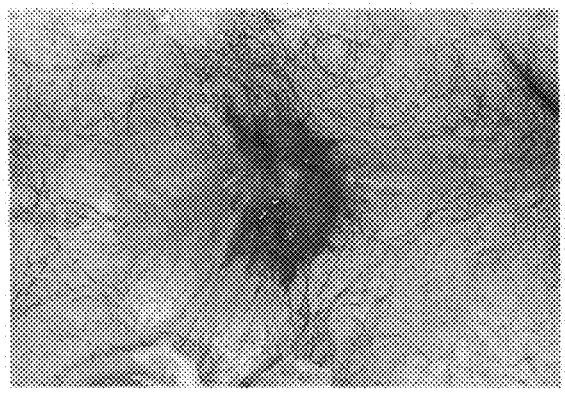
Figure 30D:
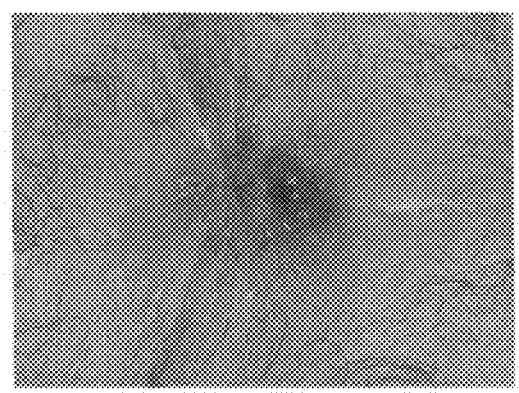

FIGS. 12a-c are photographs of the genital area of a patient afflicted with condyloma warts, as described in Example 4, before treatment;

FIGS. 13a-b are photographs of a patient afflicted with condyloma warts, as described in Example 5, following about two weeks of treatment with an exemplary cream composition according to the present invention;

FIGS. 14a-b are photographs of the genital area of a patient afflicted with condyloma warts, as described in Example 5, following about four weeks of treatment with an exemplary cream composition according to the present invention;

FIGS. 15a-b are photographs of the genital area of a patient afflicted with condyloma warts, as described in Example 6, before treatment;

FIGS. 16a-c are photographs of the genital area of a patient afflicted with condyloma warts, as described in Example 6, following about two weeks of treatment with an exemplary cream composition according to the present invention;

FIG. 17 is a photograph of the genital area of a patient afflicted with condyloma warts, as described in Example 6, following about four weeks of treatment with an exemplary cream composition according to the present invention;

FIG. 18 is a photograph of the genital area of a patient afflicted with condyloma warts, as described in Example 7, before treatment;

FIG. 19 is a photograph of the genital area of a patient afflicted with condyloma warts, as described in Example 7, following about two weeks of treatment with an exemplary cream composition according to the present invention;

FIG. 20 is a photograph of a patient afflicted with condyloma warts in the anus, as described in Example 8, before treatment;

FIG. 21 is a photograph of a patient afflicted with condyloma warts in the anus, as described in Example 8, following two days of treatment with an exemplary cream composition according to the present invention;

FIG. 22 is a photograph of a patient afflicted with condyloma warts in the anus, as described in Example 8, following about 5 weeks of treatment with an exemplary cream composition according to the present invention;

FIG. 23 is a photograph of a patient afflicted with condyloma warts in the anus, as described in Example 8, following about 8 weeks of treatment with an exemplary cream composition according to the present invention;

FIGS. 24a-b are photographs of a patient afflicted with verruca vulgaris in both hands, as described in Example 9, before treatment;

FIGS. 25a-b are photographs of a patient afflicted with verruca vulgaris in both hands, as described in Example 9, following about 3 weeks of treatment with an exemplary cream composition according to the present invention;

FIGS. 26a-b are photographs of a patient afflicted with verruca vulgaris in both hands, as described in Example 9, following about 6 weeks of treatment with an exemplary cream composition according to the present invention.

FIGS. 27a-d are photographs of the genital area of a patient afflicted with condyloma warts, as described in Example 10, before treatment (FIG. 27a) and following about 4 weeks (FIG. 27b), about 6 weeks (FIG. 27c) and about 8 weeks (FIG. 27d) treatment with an exemplary cream composition according to the present invention;

FIGS. 28a-d are photographs of the genital area of a patient afflicted with condyloma warts, as described in Example 11, before treatment (FIG. 28a) and following about 2 weeks (FIG. 28b), about 4 weeks (FIG. 28c) and about 7 weeks (FIG. 28d) treatment with an exemplary cream composition according to the present invention;

FIGS. 29a-e are photographs of the anus of a patient afflicted with condyloma warts, as described in Example 12, before treatment (FIG. 29a) and following about 2 weeks (FIG. 29b), about 5 weeks (FIG. 29c), about 8 weeks (FIG. 29d) and about 10 weeks (FIG. 29e) treatment with an exemplary cream composition according to the present invention; and FIGS. 30a-d are photographs of the anus of a patient afflicted with condyloma warts, as described in Example 13, before treatment (FIG. 30a) and following about 5 weeks (FIG. 30b), about 7 weeks (FIG. 30c) and about 9 weeks (FIG. 30d) treatment with an exemplary cream composition according to the present invention.

DESCRIPTION OF THE PREFERRED EMBODIMENTS

The present invention is of novel compositions of tellurium-containing compounds which can be efficiently used for treating skin and mucosal membrane ailments caused by HPVs. The present invention is therefore further of methods of treating such ailments, using tellurium-containing compounds. Specifically, the methods and compositions of the present invention can be used to treat any clinical manifestation of HPVs, such as, for example, common warts (e.g., verruca vulgaris), genital and venereal warts (e.g., condylomata acuminata), butcher's warts, malignant epidermodyspasia verruciformis, cervical cancer, mepidermodysplasia verruciformis, cutnaeous warts in immunosuppressed patients, laryngeal papillomas and oral papilloma.

The principles and operation of the compositions and methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As mentioned in the Background section hereinabove, tellurium-containing compounds have been described in the art as immunomodulators. A particularly effective family of tellurium-containing compounds is described, for example, in U.S. Pat. Nos. 4,752,614; 4,761,490; 4,764,461 and 4,929,739. The immunomodulating properties of this family of tellurium-containing compounds is described, for example, in U.S. Pat. Nos. 4,962,207, 5,093,135, 5,102,908 and 5,213,899, which are all incorporated by reference as if fully set forth herein.

One of the most promising compounds described in these patents is ammonium trichloro(dioxyethylene-O,O')tellurate, which is also referred to herein and in the art as AS101. As is widely described in the art, AS101, as a representative example of the family of tellurium-containing compound discussed hereinabove, exhibits potent antiviral ["Antibabesial effect of the immunomodulator AS101 in mice: role of increased production of nitric oxide". *Parasite Immunol* 1996 June; "The antitumoral effect of the immunomodulator AS101 and paclitaxel (Taxol) in a murine model of lung adenocarcinoma". *J Immunol* 1996 February; "The protective role of the immunomodulator AS101 against chemotherapy-induced alopecia studies on human and animal models". *Int J Cancer* 1996 January; and "Mechanism of radioprotection conferred by the immunomodulator AS101". *Exp Hematol* 1993 January], tumoricidal ["Effect of the immunomodulator AS101 on chemotherapy-induced multilineage myelosuppression, thrombocytopenia, and anemia in mice". *Exp Hematol* 1995 December; and "Restoration of murine cytomegalovirus (MCMV) induced myelosuppression by AS101". *Immunol Lett* 1994 December] and adjuvant activity.

It has been suggested that AS101, as well as other tellurium-containing immunomodulators, stimulate the innate and acquired arm of the immune response. It is a potent inducer of interferon (IFN) in mice ["Delay in the onset of systemic lupus erythematosus following treatment with the immunomodulator AS101: association with IL-10 inhibition and increase in TNF-alpha levels". *J Immunol* 1997 *September*; "The immunomodulator AS-101 inhibits IL-10 release and augments TNF alpha and IL-1 alpha release by mouse and human mononuclear phagocytes". *Cell Immunol* 1997 *March*; "The antitumoral effect of the immunomodulator AS101 and paclitaxel (Taxol) in a murine model of lung adenocarcinoma". *J Immunol* 1996 *February*] and humans ["Effect of the immunomodulator AS101 on chemotherapy-induced multilineage myelosuppression, thrombocytopenia, and anemia in mice". *Exp Hematol* 1995 *December*].

AS101, as well as other tellurium-containing immunomodulators, have also been shown to induce the secretion of a spectrum of cytokines, such as IL-1, IL-6 and TNF-α. The macrophages have been characterized as the main target for AS101 ["Up-regulation by ammonium trichloro(dioxoethylene-0,0') tellurate (AS101) of Fas/Apo-1 expression on B16 melanoma cells: implications for the antitumor effects of AS101". *J Immunol* 1998 *October*] and it found to inhibit IL-10 at the m-RNA level while increasing at the same time the IL-12.

Other publications describing the immunomodulation properties of AS101 include, for example, "The immunomodulator AS101 restores T(H1) type of response suppressed by *Babesia rodhaini* in BALB/c mice". *Cell Immunol* 1998 *February*; "Predominance of TH1 response in tumor-bearing mice and cancer patients treated with AS101". *J Natl Cancer Inst* 1996 *September*; "AS-101: a modulator of in vitro T-cell proliferation". *Anticancer Drugs* 1993 *June*; "The immunomodulator AS101 administered orally as a chemoprotective and radioprotective agent". *Int J Immunopharmacol* 1992 *May*; "Inhibition of the reverse transcriptase activity and replication of human immunodeficiency virus type 1 by AS101 in vitro". *AIDS Res Hum Retroviruses* 1992 *May*; "Immunomodulatory effects of AS101 on interleukin-2 production and T-lymphocyte function of lymphocytes treated with psoralens and ultraviolet A". *Photodermatol Photoimmunol Photomed* 1992 *February*; "Use and mechanism of action of AS101 in protecting bone marrow colony forming units-granulocyte-macrophage following purging with ASTA-Z 7557". *Cancer Res* 1991 *Oct*. 15; "The effect of the immunomodulator agent AS101 on interleukin-2 production in systemic lupus erythematosus (SLE) induced in mice by a pathogenic anti-DNA antibody". *Clin Exp Immunol* 1990 *March*; "Toxicity study in rats of a tellurium based immunomodulating drug, AS-101: a potential drug for AIDS and cancer patients". *Arch Toxicol* 1989; "The biological activity and immunotherapeutic properties of AS-101, a synthetic organotellurium compound". *Nat Immun Cell Growth Regul* 1988; and "A new immunomodulating compound (AS-101) with potential therapeutic application". *Nature* 1987 *November*

AS101, as well as other tellurium-containing immunomodulators, are therefore capable of skewing the immune response towards a Th1 phenotype. This type of response is crucial against intracellular pathogens such as viruses.

Furthermore, toxicity tests have showed that LD50 values in rats following intravenous and intramuscular dosage of AS101 are 500-1000 folds higher than the immunology effective dose. These tellurium-containing compounds are therefore further characterized as substantially non-toxic.

Based on these findings, while conceiving the present invention, it was envisioned that since AS101 is a potent modulator of the immune response from Th2 to Th1 response, and is further characterized as a substantially non-toxic agent, this tellurium-containing compound, as well as other tellurium compounds of this family, could serve as potent therapeutic agents against infections caused by HPV, devoid of the disadvantages associated with the presently known agents for treating HPV infections described hereinabove.

It should be noted in this respect that although AS101 has been shown to exert an anti-viral activity, in studies conducted heretofore, its efficacy as an anti-viral agent against human viruses was found to be insufficient.

As is further mentioned hereinabove, another class of tellurium-containing compounds has been recently disclosed in U.S. Provisional Patent Application No. 60/610,660. As taught in this patent application, this class of tellurium compounds was also shown to exert immunomodulating properties and therefore, it was further envisioned that these compounds could also serve as potent therapeutic agents against infections caused by HPV.

As is demonstrated in the Examples section that follows, while reducing the present invention to practice, it was indeed found that treating human patients afflicted with various HPV infections with a tellurium-containing compound such as AS101 was highly efficient, resulting in high treatment responsiveness and minimized side effects.

Hence, according to one aspect of the present invention there is provided a method of treating a skin or mucosal membrane ailment caused by HPV, which is effected by administering to a subject in need thereof a therapeutically effective amount of one or more tellurium-containing compounds.

As used herein, the phrase "tellurium-containing compound" encompasses any compound that includes one or more tellurium atoms and exhibits immunomodulating properties.

The phrase "immunomodulating properties" includes any effect of the compound on the immune response of a subject. Exemplary immunomodulating properties can be manifested, for example, by an effect on cytokines secretion, interleukins production, lymphocytes function, and the like.

The compound can be, for example, an inorganic tellurium-containing compound such as, for example, tellurium dioxide ($TeO_2$), halogenated tellurium, sulfonated tellurium, phosphorylated tellurium, as well as salts thereof (e.g., ammonium salts, alkaline salts, phosphonium salts and the like) and any complexes thereof.

The compound can alternatively be an organic tellurium-containing compound which includes one or more tellurium atoms and one or more organic moieties that are attached thereto.

Representative examples of inorganic tellurium-containing compounds that were shown to exert immunomodulating properties and hence are particularly useful in the context of the present invention include, for example, $TeO_2$ and $TeX_4$, wherein X is halogen.

As used herein, the term "halogen", which is also referred to herein interchangeably as "a halogen atom" or "halo", includes chloro (Cl), bromo (Br), iodo (I) and fluoro (F).

Also included are compounds that form $TeO_2$ in aqueous solutions, preferably in the form of a complex such as, for example, a $TeO_2$ complex with citric acid or ethylene glycol. A representative example of the latter is the complex $TeO_2.HOCH_2CH_2OH.NH_4Cl$.

Organic tellurium-containing compounds that were shown to exert immunomodulating properties and hence are particularly useful in the context of the present invention include, for example, ammonium salts, or any other salts, of halogenated tellurium-containing compounds having a bidentate cyclic moiety attached to the tellurium atom. The bidentate cyclic moiety is preferably a di-oxo moiety having two oxygen atoms attached to the tellurium atom. Alternatively, the bidentate cyclic moiety can be a di-thio moiety, in which two sulfur atoms are attached to the tellurium atom.

Preferred compounds in this category are collectively represented by the general Formula I:

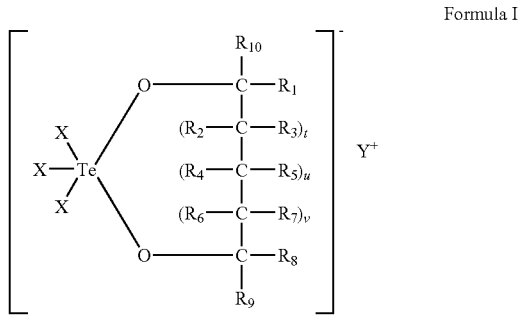

Formula I

In the general Formula I above, each of t, u and v is independently 0 or 1, such that the compound may include a five-membered ring, a six-membered ring, a seven-membered ring or an eight-membered ring. Preferably, each of t, u and v is 0, such that the compound includes a five-membered ring.

X is a halogen atom, as described hereinabove, and is preferably chloro.

Y is selected from the group consisting of ammonium, phsophonium, potassium, sodium and lithium, and is preferably ammonium.

each of $R_1$-$R_{10}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, sulfonamide, phosphonyl, phosphinyl, carbonyl, thiocarbonyl, carboxy, thiocarboxy, carbamate, thiocarbamate, amido, sulfonamido, and amino, as these terms are defined herein.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

The term "haloalkyl" refers to an alkyl, as this term is defined herein, substituted by a halogen, as defined herein, and includes, for example, chloromethyl, 2-iodoethyl, 4-bromo-n-butyl, iodoethyl, 4-bromo-n-pentyl and the like.

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylalkyl" refers to an alkyl, as this term is defined herein, substituted by a carbonyl group, as defined herein, and includes, for example, methanoylmethyl, ethanoylethyl and the like.

The term "amidoalkyl" refers to an alkyl, as this term is defined herein, substituted by an amide group, as defined herein, and includes, for example, —$CH_2CONH_2$; —$CH_2CH_2CONH_2$; —$CH_2CH_2CH_2CONH_2$ and the like.

The term "cyanoalkyl" refers to an alkyl, as this term is defined herein, substituted by an cyano group, as defined herein, and includes, for example, —$CH_2CN$; —$CH_2CH_2CN$; —$CH_2CH_2CH_2CN$ and the like.

The term "N-monoalkylamidoalkyl" refers to an alkyl, as this term is defined herein, substituted by an amide group, as defined herein, in which one of R' and R" is an alkyl, and includes, for example, —$CH_2CH_2CONHCH_3$, and —$CH$—$_2CONHCH_2CH_3$.

The term N,N-dialkylamidoalkyl refers to an alkyl, as this term is defined herein, substituted by an amide group, as defined herein, in which both R' and R" are alkyl, and includes, for example, —$CH_2CON(CH_3)_2$; $CH_2CH_2CON(CH_2$—$CH_3)_2$ and the like.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, phosphonyl, phosphinyl, carbonyl, thiocarbonyl, carboxy, thiocarboxy, carbamate, thiocarbamate, amido, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein. Representative examples are piperidine, piperazine, tetrahydro furane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "carboxy" group refers to a —C(=O)—O—R' or a —O—C(=O)—R' group, where R' is as defined herein.

A "sulfinyl" group refers to an —S(=O)—R' group, where R' is as defined herein.

A "sulfonyl" group refers to an —S(=O)$_2$—R' group, where R' is as defined herein.

A "sulfate" group refers to a —O—S(=O)$_2$—OR' group, where R' is as defined herein.

A "sulfonamido" group refers to a —S(=O)$_2$—NR'R" group or a R'S(=O)$_2$—NR", with R' is as defined herein and R" is as defined for R'.

A "carbamyl" or "carbamate" group refers to an —OC(=O)—NR'R" group or a R"OC(=O)—NR'— group, where R' and R" are as defined herein.

A "thiocarbamyl" or "thiocarbamate" group refers to an —OC(=S)—NR'R" group or an R"OC(=S)NR'— group, where R' and R" are as defined herein.

An "amino" group refers to an —NR'R" group where R' and R" are as defined herein.

An "amido" group refers to a —C(=O)—NR'R" group or a R'C(=O)—NR" group, where R' and R" are as defined herein.

A "nitro" group refers to an —NO$_2$ group.

A "cyano" group refers to a —C≡N group.

The term "phosphonyl" describes a —O—P(=O)(OR')(OR") group, with R' and R" as defined hereinabove.

The term "phosphinyl" describes a —PR'R" group, with R' and R" as defined hereinabove.

As cited hereinabove, the compounds in this category are salts of organic tellurium-containing compounds. The salts can be, for example, ammonium salts, phsophonium salts and alkaline salts such as potassium salts, sodium salts, lithium salts and the like.

Hence, Y in Formula I above can be a phosphonium group, as defined herein, an ammonium group, as defined herein, potassium (K$^+$), sodium (Na$^+$) or lithium (Li$^+$).

As used herein, the term "phosphonium" describes a —P$^+$R'R"R'" group, with R' and R" as defined herein and R'" is as defined for R'. The term "phsophonium", as used herein, further refers to a —P$^+$R$_6$ group, wherein each of the six R substituents is independently as defined herein for R, R" and R'".

The term "ammonium" describes a —N$^+$R'R"R'" group, with R', R" and R'" as defined herein.

More preferred compounds in this category include compounds having the general Formula I described above, in which Y is ammonium or phosphonium, t, u and v are each 0, each of R$_1$-R$_9$ is hydrogen and R$_{10}$ is hydrogen or alkyl. These compounds can be represented by the following structure:

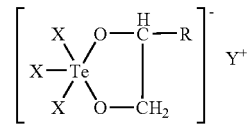

wherein R is hydrogen or alkyl, preferably methyl, and X is halogen, preferably chloro.

The presently most preferred compound for use in the context of the present invention has the following structure:

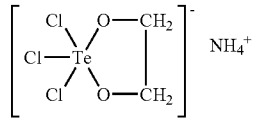

This compound is ammonium trichloro(dioxyethylene-O, O')tellurate, which is also referred to herein and in the art as AS101.

An additional exemplary compound in this category is:

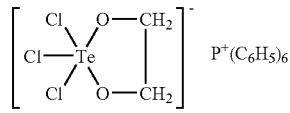

Additional representative examples of organic tellurium-containing compound that are suitable for use in the context of the present invention include halogenated tellurium having a bidentate cyclic moiety attached to the tellurium atom. The bidentate cyclic moiety is preferably a di-oxo ligand having two oxygen atoms attached to the tellurium atom. Alternatively, the bidentate cyclic moiety can be a di-thio ligand, in which two sulfur atoms are attached to the tellurium atom.

Preferred compounds in this category can be represented by the general Formula II:

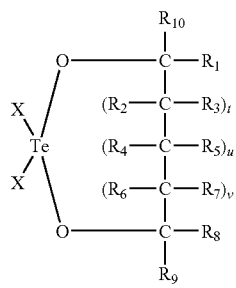

Formula II wherein t, u, v, X and $R_1$-$R_{10}$ are as defined hereinabove.

More preferred compounds are those in which t, u, and v are each 0, and X is chloro, such as, but not limited to, the compound having the following structure:

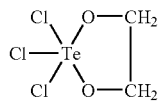

The organic tellurium-containing compounds having Formulae I and II can be readily prepared by reacting tetrahalotelluride such as $TeCl_4$ with a dihydroxy compound, as is described in detail in U.S. Pat. Nos. 4,752,614, 4,761,490, 4,764,461 and 4,929,739.

Additional representative examples of organic tellurium-containing compound that are suitable for use in the context of the present invention include compounds in which two bidentate cyclic moieties are attached to the tellurium atom. Preferably, each of the cyclic moieties is a di-oxo moiety. Alternatively, one or more of the cyclic moieties is a di-thio moiety.

Preferred compounds in this category are collectively represented by the general Formula III:

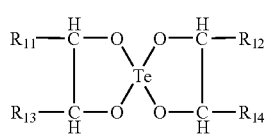

Formula III wherein each of $R_{11}$-$R_{14}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido, as these terms are defined herein.

More preferred compounds in this category are those in which each of $R_{11}$-$R_{14}$ is hydrogen.

Additional representative examples of organic tellurium-containing compounds that are suitable for use in the context of the present invention include the recently disclosed bis-tellurium compounds having general Formula IV:

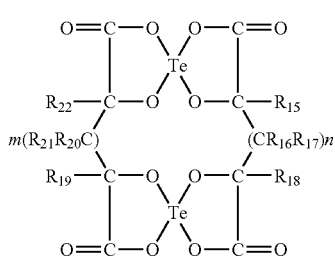

Formula IV wherein each of $R_{15}$-$R_{22}$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, alkoxy, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido, as these terms are defined herein; and m and n are each an integer from 0 to 3.

Preferred compounds in this category are those in which m and n are each 0.

The presently most preferred compound in this family is a compound in which $R_{15}$, $R_{18}$, $R_{19}$ and $R_{22}$ are all hydrogen, and which has the following structure:

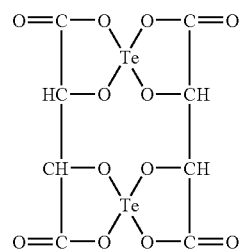

Compounds having the general Formula IV can be readily prepared by reacting substantially equimolar amounts of a tellurium tetralkoxide and a polycarboxylic acid. These materials are combined in the presence of a water free organic solvent such as dried ethanol, dimethyl sulfoxide, i-propanol and the like. Generally the reaction may take place at ambient conditions but if desired higher or lower temperatures and higher or lower pressures may be utilized.

Exemplary tellurium tetraalkoxide compounds that are usable in the preparation of the compounds having general Formula IV above include, without limitation, tetramethoxide, tetraethoxide, tetrapropoxide, tetraisopropoxide, tetrabutoxide, and tetrapentoxide tellurium compounds.

Useful polycarboxylic acids include also polyhydroxy polycarboxylic and hydroxy polycarboxylic acids. Exemplary polycarboxylic acids that are usable in the preparation of the compounds having general Formula IV above include, without limitation, tartaric acid, glutaric acid, succinic acid, malonic acid, gluconic acid and the like.

Additional organic tellurium-containing compounds that are suitable for use in the context of the present invention include those having the general Formula V:

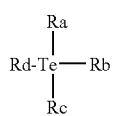

Formula V wherein each of Ra, Rb, Rc and Rd is independently selected from the group consisting of halogen alkyl, aryl, cycloalkyl, alkoxy, aryloxy, thioalkoxy, thioaryloxy, carboxy, carbonyl, thiocarboxy, thiocarbonyl, carbamyl, and thiocarbamyl, as these terms are defined hereinabove, whereby at least one of Ra-Rd is not halogen, namely, is selected from the group consisting of alkyl, aryl, cycloalkyl, alkoxy, aryloxy, thioalkoxy, thioaryloxy, carboxy, carbonyl, thiocarboxy, thiocarbonyl, carbamyl, and thiocarbamyl.

Compounds in this category include those in which one of Ra, Rb, Rc and Rd is halogen alkyl, aryl, cycloalkyl, alkoxy, aryloxy, thioalkoxy, thioaryloxy, carboxy, carbonyl, thiocarboxy, thiocarbonyl, carbamyl, or thiocarbamyl, whereby the others halogen atoms, e.g., chloro.

Other compounds in this category include those in which two or three of Ra, Rb, Rc and Rd are as described above and the others are halogens e.g., chloro.

Other compounds in this category include those in which each of Ra, Rb, Rc and Rd is as described hereinabove.

An exemplary compound in this category is $PhTeCl_3$.

The compounds described above can be administered or otherwise utilized in this and other aspects of the present invention, either as is or as a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

As is demonstrated in the Examples section that follows, AS101, a representative example of a tellurium-containing compound according to the present invention, was found to be highly efficient in treating various ailments caused by various HPVs, including verruca vulgaris and genital and anus condylomata acuminata. The treatment was accompanied with minimal or no adverse side effects and the ailments (e.g., warts) were substantially completely removed.

The high efficiency of the treatment according to the present invention, as compared with the presently known methods of treating HPV-caused ailments, is attributed to the immunomodulating and anti-viral activity of the tellurium-containing compounds described above. As such, treatment with the tellurium-containing compounds described above, affects not only the manifested visible lesions but rather suppress the cause of the ailment—the virus itself. As a result, viral particles that may be lurking in normal-appearing areas surrounding the warts, are also destroyed. This effect of the tellurium-containing compounds described herein is clearly demonstrated in, for example, FIGS. 13a and 13b, where it can be seen that the area affected by the treatment (seen as black spots) is larger that the visible lesion area before treatment (see, FIGS. 12a-c).

The method according to this aspect of the present invention can therefore be efficiently utilized for treating skin and mucosal membrane ailments caused by a HPV.

As used herein, the phrase "a skin or mucosal membrane ailment caused by a HPV", which also referred to herein interchangeable as "HPV-caused ailment", encompasses any ailment that is associated, either directly or indirectly, with any type of HPV As is discussed hereinabove, to date, there are more than seventy identified distinct types of HPVs. These different types have been subdivided into two large categories: cutaneous and mucosal. Since, as is further discussed hereinabove, some HPV-caused ailments may develop into cervical cancer, these different virus types have been further categorized in this respect by their risk grade and therefore include low-risk HPV types, moderate-risk HPV types and high-risk HPV types.

According to an embodiment this aspect of the present invention, the method described above is therefore further directed at treating moderate-risk and high-risk FPV types and thus at treating and preferably preventing the development of cancer.

Exemplary skin and mucosal membrane ailments that are treatable by the method of this aspect of the present invention therefore include verruca vulgaris, plantar warts, palmar warts, periungal warts, planar warts, mosaic warts, genital warts, venereal warts (condylomata acuminata), butcher's warts, malignant epidermodyspasia verruciformis, advanced intraepithelial dysplasia, cervical cancer, mepidermodysplasia verruciformis, cutnaeous warts in immunosuppressed patients, laryngeal papillomas and oral papilloma.

The various ailments caused by HPVs are typically manifested in various skin areas and mucosal membranes, including, for example, hands, face, forearms, elbows, legs, nails and anus, and genital areas such as the perianal area, perineum, vulva, penis, vagina, and in rare severe cases the cervix. Although rare, HPV-caused ailments can be also manifested on the oral mucosa, conjunctivae and larynx.

The compounds described above can be administered to a subject afflicted by an HPV-caused ailment by any of various systemic routes.

Suitable routes of systemic administration may, for example, include the inhalation, oral, buccal, rectal, transmucosal, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject of the present invention.

When administering systemically, a therapeutically effective amount of the tellurium-containing compounds described herein may range, for example, from about 0.01 $mg/m^2/day$ to about 10.0 $mg/m^2/day$ and thus can be for example, 0.01 $mg/m^2/day$, 0.02 $mg/m^2/day$, 0.03 $mg/m^2/day$, 0.04 $mg/m^2/day$, 0.05 $mg/m^2/day$, 0.06 $mg/m^2/day$, 0.07 $mg/m^2/day$, 0.08 $mg/m^2/day$, 0.09 $mg/m^2/day$ and 0.1 $mg/m^2/day$. Preferably, when administered parenterally, the therapeutically effective amount is 0.1 $mg/m^2/day$ and higher and thus can be, for example, 0.2 $mg/m^2/day$, 0.3 $mg/m^2/day$, 0.4 $mg/m^2/day$, 0.5 $mg/m^2/day$, 0.6 $mg/m^2/day$, 0.7 $mg/m^2/day$, 0.8 $mg/m^2/day$, 0.9 $mg/m^2/day$, 1.0 $mg/m^2/day$, 2.0 $mg/m^2/day$, 3.0 $mg/m^2/day$, 4.0 $mg/m^2/day$, 5.0 $mg/m^2/day$, and up to 10.0 $mg/m^2/day$. When administered orally, a daily dose typically ranges between 10 mg and 150 mg.

As used herein, the term "about" refers to ±10%.

Optionally and preferably, the compounds described above can be administered to a subject afflicted by an HPV ailment by local routes, and more preferably, the compounds are administered topically.

Topical application of the tellurium-containing compounds described herein is preferably effected by applying onto a treated skin or mucosal membrane area a therapeutically effective amount the compound.

The treated area can be, for example, hands, face, forearms, elbows, legs, nails, anus, and genital areas such as the perianal area, perineum, vulva, penis, vagina, and if needed, the cervix.

Herein, the phrase "treated area" encompasses the affected area (e.g., the wart(s)) as well as the tissues surrounding the indicated area. The topical application is effected on and around the clinical manifestation (e.g., the wart(s)).

The method according to this aspect of the present invention can further comprise, in addition to administering the tellurium-containing compounds described above, co-administration of an additional active agent. The co-administration can be effected prior to, concomitant with or subsequent to the administration of the tellurium-containing compound. The additional active agent is used for providing an additive beneficial effect in terms of the ailment being treated, conditions associated with the ailment being treated or other parameters such as psychological effects and prophylactic effects.

Hence, exemplary additional active agents according to this embodiment of present invention include, without limitation, one or more, or any combination of an antibiotic agent, an antimicrobial agent, an anti-acne agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, a chemotherapeutic agent, an antidepressant, an anti histamine, a vitamin, a hormone and an anti-dandruff agent.

Suitable anti-acne agents for use in this context of the present invention include, without limitation, keratolytics such as salicylic acid, sulfur, glycolic, pyruvic acid, resorcinol, and N-acetylcysteine and retinoids such as retinoic acid and its derivatives (e.g., cis and trans, esters).

Suitable antibiotics for use in this context of the present invention include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable antipruritic agents include, without limitation, pharmaceutically acceptable salts of methdilazine and trimeprazine.

Non-limiting examples of anesthetic drugs that are suitable for use in context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Suitable antimicrobial agents, including antibacterial, antifungal, antiprotozoal and antiviral agents, for use in context of the present invention include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs"), corticotropin-releasing factor (CRF) antagonists, α-adrenoreceptor antagonists, NK1-receptor antagonists, $5-HT_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Exemplary anti-dandruff ingredients usable in context of the present invention include, without limitation, zinc pyrithione, shale oil and derivatives thereof such as sulfonated shale oil, selenium sulfide, sulfur; salicylic acid, coal tar, povidone-iodine, imidazoles such as ketoconazole, dichlorophenyl imidazolodioxalan, clotrimazole, itraconazole, miconazole, climbazole, tioconazole, sulconazole, butoconazole, fluconazole, miconazolenitrite and any possible stereo isomers and derivatives thereof such as anthralin, piroctone olamine (Octopirox), selenium sulfide, and ciclopirox olamine, and mixtures thereof.

Non-limiting examples of vitamins usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of dermatological active ingredients usable in context of the present invention include jojoba oil and aromatic oils such as methyl salicylate, wintergreen, peppermint oil, bay oil, eucalyptus oil and citrus oils, as well as ammonium phenolsulfonate, bismuth subgallate, zinc phenolsulfonate and zinc salicylate. Non-limiting examples of antifungal agents include miconazole, clotrimazole, butoconazole, fenticonasole, tioconazole, terconazole, sulconazole, fluconazole, haloprogin, ketonazole, ketoconazole, oxinazole, econazole, itraconazole, terbinafine, nystatin and griseofulvin.

Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

In addition to the above, the treatment of an HPV-caused ailment according to the present invention may be combined with other treatment methods known in the art (i.e., combination therapy). Thus, the method according to this aspect of the present invention may further involve additional treatment by any of the methods described above for treating HPV infections. The tellurium-containing compounds described above can thus be, for example, co-administered (simultaneously or separately) with additional agents for treating HPVs infections such as, for example, salicylic acid, 5-fluoruracil and the like. Alternatively, the method described above can be accompanied by any of the physical treatment methods described above (e.g., laser therapy, NO therapy and the like).

In any of the different embodiments of the method according to this aspect of the present invention, the tellurium-containing compounds described herein can be provided to a subject either per se, or as part of a pharmaceutical composition where it is mixed with a pharmaceutically acceptable carrier.

Hence, according to another aspect of the present invention there is provided a pharmaceutical composition, which comprises a tellurium-containing compound as described herein and a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

As described above, suitable routes of systemic administration may, for example, include oral, rectal, transmucosal, transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As is further described above, a suitable route of administering the tellurium-containing compounds of the present invention include topical application.

Hence, in a preferred embodiment of the present invention, the pharmaceutical composition is formulated in a form suitable for topical application on the treated area.

As used herein, the phrase "topical application" describes application onto a biological surface, whereby the biological surface include, for example, a skin area (e.g., hands, forearms, elbows, legs, face, nails, anus and genital areas as described above) or a mucosal membrane.

By selecting the appropriate carrier and optionally other ingredients that can be included in the composition, as is detailed hereinbelow, the compositions of the present invention may be formulated into any form typically employed for topical application. Hence, the compositions of the present invention can be, for example, in a form of a cream, an ointment, a paste, a gel, a lotion, a milk, a suspension, an aerosol, a spray, a foam, a shampoo, a hair conditioner, a serum, a swab, a pledget, a pad, a patch and a soap.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy,* 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy*, supra, for further information.

Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base.

Additional reference may be made to *Remington: The Science and Practice of Pharmacy*, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition.

Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions.

Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

When the pharmaceutical composition according to the present invention is formulated for topical application, the concentration of the tellurium-containing compound preferably ranges from about 0.01 weight percent and about 50 weight percents from the total weight of the composition.

Thus, depending on the condition being treated and the composition form, the concentration of the tellurium-containing compound can be, for example, 0.01 weight percent, 0.05 weight percent, 0.1 weight percent, 0.5 weight percent, 1 weight percent, 2 weight percents, 3 weight percents, 4 weight percents or 5 weight percents. Preferably, the concentration of the tellurium-containing compound is 5 weight percents and higher and thus can be, for example, 5 weight percents, 6 weight percents, 7 weight percents, 8 weight percents, 9 weight percents or 10 weight percents. 10 weight percents and higher and therefore can be, for example, 11 weight percents, 12 weight percents, 13 weight percents, 14 weight percents, 15 weight percents, 16 weight percents, 17 weight percents, 18 weight percents, 19 weight percents, 20 weight percents, 21 weight percents, 22 weight percents, 23 weight percents, 24 weight percents and up to 25 weight percents of the total weight of the composition. Alternatively, the concentration of the tellurium-containing compound is higher than 25 weight percents and can be up to 50 weight percents of the total weight of the composition.

Each of the pharmaceutical compositions described herein may further comprise, according to an embodiment of the present invention an additional active agent, as described hereinabove.

Each of the pharmaceutical compositions described herein can optionally further comprise a variety of components that are suitable for providing the compositions with additional usage benefits. Such conventional optional components are well known to those skilled in the art and are referred to herein as "ingredients". Some non-limiting representative examples of these ingredients include humectants, deodorants, antiperspirants, sun screening agents, sunless tanning agents, hair conditioning agents, pH adjusting agents, chelating agents, preservatives, emulsifiers, occlusive agents, emollients, thickeners, solubilizing agents, penetration enhancers, antiirritants, colorants, propellants (as described above) and surfactants.

Thus, for example, the compositions of the present invention can comprise humectants or moisturizing agents. Representative examples of humectants that are usable in this context of the present invention include, without limitation, guanidine, glycolic acid and glycolate salts (e.g. ammonium slat and quaternary alkyl ammonium salt), aloe vera in any of its variety of forms (e.g., aloe vera gel), allantoin, urazole, polyhydroxy alcohols such as sorbitol, glycerol, hexanetriol, propylene glycol, butylene glycol, hexylene glycol and the like, polyethylene glycols, sugars and starches, sugar and starch derivatives (e.g., alkoxylated glucose), hyaluronic acid, lactamide monoethanolamine, acetamide monoethanolamine and any combination thereof.

The compositions of the present invention can further comprise a pH adjusting agent. The addition of a pH adjusting agent is particularly preferred when the compositions are applied topically on the skin or in the genital areas. The pH of these treated areas is typically lower than 6.0. Hence, it is preferable for the compositions of the present invention to have a pH value of between about 4 and about 7, preferably between about 4 and about 6, so as to avoid irritations to the skin or induction of imbalance of the bacteria population if the genital areas. Suitable pH adjusting agents include, for example, one or more of adipic acids, glycines, citric acids, calcium hydroxides, magnesium aluminometasilicates, buffers or any combinations thereof.

Representative examples of deodorant agents that are usable in the context of the present invention include, without limitation, quaternary ammonium compounds such as cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmlthyl sarcosine, lauroyl sarcosine, N-myristoyl glycine, potassium N-lauryl sarcosine, stearyl, trimethyl ammonium chloride, sodium aluminum chlorohydroxy lactate, tricetylmethyl ammonium chloride, 2,4,4'-trichloro-2'-hydroxy diphenyl ether, diaminoalkyl amides such as L-lysine hexadecyl amide, heavy metal salts of citrate, salicylate, and piroctose, especially zinc salts, and acids thereof, heavy metal salts of pyrithione, especially zinc pyrithione and zinc phenolsulfate. Other deodorant agents include, without limitation, odor absorbing materials such as carbonate and bicarbonate salts, e.g. as the alkali metal carbonates and bicarbonates, ammonium and tetraalkylammonium carbonates and bicarbonates, especially the sodium and potassium salts, or any combination of the above.

Antiperspirant agents can be incorporated in the compositions of the present invention either in a solubilized or a particulate form and include, for example, aluminum or zirconium astringent salts or complexes.

Representative examples of sun screening agents usable in context of the present invention include, without limitation, p-aminobenzoic acid, salts and derivatives thereof (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic acid and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoylmethane, and any combination thereof.

Representative examples of sunless tanning agents usable in context of the present invention include, without limitation, dihydroxyacetone, glyceraldehyde, indoles and their derivatives. The sunless tanning agents can be used in combination with the sunscreen agents.

The chelating agents are optionally added to the compositions of the present invention so as to enhance the preservative or preservative system. Preferred chelating agents are mild agents, such as, for example, ethylenediaminetetraacetic acid (EDTA), EDTA derivatives, or any combination thereof.

Suitable preservatives that can be used in the context of the present composition include, without limitation, one or more alkanols, disodium EDTA (ethylenediamine tetraacetate), EDTA salts, EDTA fatty acid conjugates, isothiazolinone, parabens such as methylparaben and propylparaben, propylene glycols, sorbates, urea derivatives such as diazolindinyl urea, or any combinations thereof.

Suitable emulsifiers that can be used in the context of the present invention include, for example, one or more sorbitans, alkoxylated fatty alcohols, alkylpolyglycosides, soaps, alkyl sulfates, monoalkyl and dialkyl phosphates, alkyl sulphonates, acyl isothionates, or any combinations thereof.

Suitable occlusive agents that can be used in the context of the present invention include, for example, petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Suitable emollients, that can be used in the context of the present invention include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Suitable thickeners that can be used in the context of the present invention include, for example, non-ionic water-soluble polymers such as hydroxyethylcellulose (commercially available under the Trademark Natrosol® 250 or 350), cationic water-soluble polymers such as Polyquat 37 (commercially available under the Trademark Synthalen® CN), fatty alcohols, fatty acids and their alkali salts and mixtures thereof.

Representative examples of solubilizing agents that are usable in this context of the present invention include, without limitation, complex-forming solubilizers such as citric acid, ethylenediamine-tetraacetate, sodium meta-phosphate, succinic acid, urea, cyclodextrin, polyvinylpyrrolidone, diethylammonium-ortho-benzoate, and micelle-forming solubilizers such as TWEENS and spans, e.g., TWEEN 80. Other solubilizers that are usable for the compositions of the present invention are, for example, polyoxyethylene sorbitan fatty acid ester, polyoxyethylene n-alkyl ethers, n-alkyl amine n-oxides, poloxamers, organic solvents, phospholipids and cyclodextrines.

Suitable penetration enhancers usable in context of the present invention include, but are not limited to, dimethylsulfoxide (DMSO), dimethyl formamide (DMF), allantoin, urazole, N,N-dimethylacetamide (DMA), decylmethylsulfoxide ($C_{10}$ MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil. Such oils include, for example, safflower oil, cottonseed oil and corn oil.

Suitable anti-irritants that can be used in the context of the present invention include, for example, steroidal and non steroidal anti-inflammatory agents or other materials such as aloe vera, chamomile, alpha-bisabolol, cola nitida extract, green tea extract, tea tree oil, licoric extract, allantoin, caffeine or other xanthines, glycyrrhizic acid and its derivatives.

The compositions of the present invention may be packed or presented in any convenient way. For example, they may be packed in a tube, a bottle, or a pressurized container, using techniques well known to those skilled in the art and as set forth in reference works such as Remington's Pharmaceutical Science $15^{th}$ Ed. It is preferred that the packaging is done in such a way so as to minimize contact of the unused compositions with the environment, in order to minimize contamination of the compositions before and after the container is opened.

The compositions are preferably identified in print, in or on the packaging material, for use in the treatment an ailment caused by HPV, as described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of Compositions Containing Tellurium Compounds

Compositions for topical or systemic application, which contain one or more of the tellurium compounds described herein and optionally pharmaceutically acceptable carriers and excipients, are formulated as creams, lotions, ointments, gels, solutions, foams, mousses and the like (as is detailed hereinabove), using conventional methods (see, for example, (see, for example, Harry's Cosmeticology, Seventh Edition, Edited by JB Wilkinson and RJ Moore, Longmann Scientific & Technical, 1982, Chapter 13 "The Manufacture of Cosmetics" pages 757-799; and "Remington's Pharmaceutical Sciences," Mack Publishing Co., Easton, Pa., latest edition).

Exemplary compositions for topical application according to the present invention were prepared in the form of a cream as follows:

Preparation of Composition 1

Forty (40) grams of a powdered ammonium trichloro(dioxoethylene-O,O')tellurate (AS-101, manufactured under GLP by IMI (TAMI) Institute for Research & Development Ltd., Israel) were dissolved in 100 ml dimethyl sulfoxide, so as to make a 40% w/w solution. The solution was then combined with an equal weight of petrolatum, U.S.P. (e.g., Intensive Vaseline cream) so as to make a cream containing about 17%-20% by weight of the tellurate.

Preparation of Composition 2

Composition 2 was prepared as described above for Composition 1, with the addition of 6% by weight of salicylic acid.

Another exemplary composition according to the present invention was prepared in the form of a solution, which can be administered as drops, as follows:

Preparation of Composition 3

10 grams of ammonium trichloro(dioxoethylene-O,O')tellurate (AS-101) were dissolved in 90 grams DMSO to thereby form a 10% solution of AS-101.

Example 2

Treatment of Condyloma Acuminatum with a Tellurium Composition

A human patient with condyloma acuminatum in the perianal region was treated with Composition 1 (described in Example 1 hereinabove) by topically applying the composition twice daily on and around the affected area for a period of about 4 weeks.

Following a few days of treatment the lesion changed color from pink to grey-black and following about 4 to 5 weeks, the lesion substantially sloughed off without leaving any scarring. FIGS. 1-5 present images of the treated area, which show the effect of the therapy on the condyloma at bi-weekly intervals during the period of treatment.

Example 3

Treatment of Verruca with a Tellurium Composition

Figure 6:
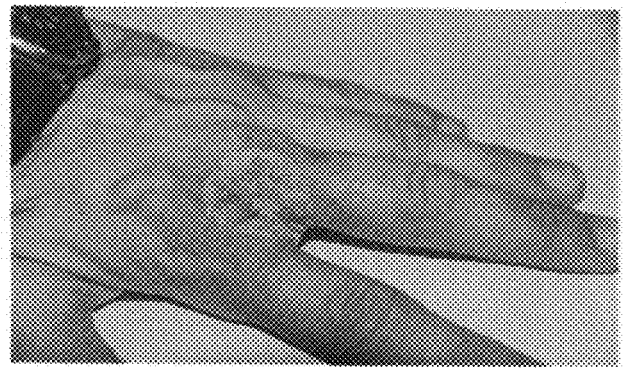
Figure 7:
Figure 8:
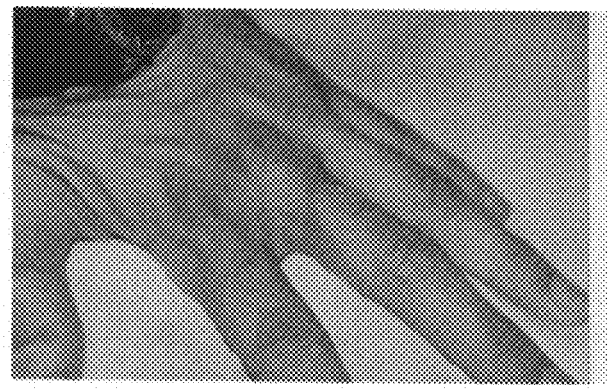

A human patient with a verrucca lesion on the hand was treated with Composition 3 described in Example 1 hereinabove. The formulation was applied on and around the affected area twice daily for a period of about 10 weeks. FIGS. 6-8 present images showing the progress of treatment at bi-weekly intervals. As is shown in, for example, FIG. 8, at the end of the period of treatment, the wart substantially sloughed off, leaving no scar on the treated area.

Example 4

Treatment of Verruca with a Tellurium Composition

Figure 9:
Figure 10:
Figure 11:
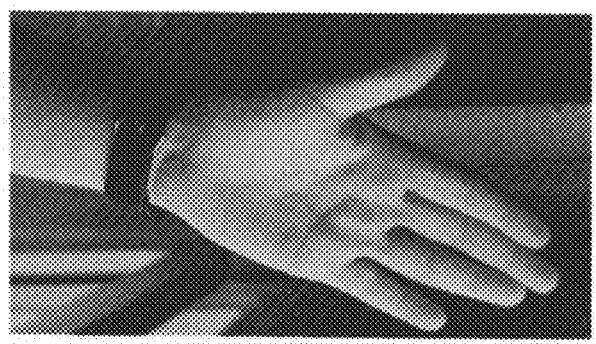

A human patient with multiple verrucca lesions on the hand was treated with Composition 3 described in Example 1 hereinabove. The formulation was applied twice daily for a period of about 4 weeks. FIGS. 9-11 present images showing the progress of treatment at biweekly intervals. As is shown in, for example, FIG. 11, at the end of the period of treatment, the wart substantially sloughed off, leaving no scar on the treated area.

Example 5

Treatment of Condyloma Acuminatum with a Tellurium Composition

A 26-years old female with condyloma acuminata in the genital region was treated with Composition 1 (described in Example 1 hereinabove) by topically applying the composition twice daily on and around the affected area for a period of about 4 weeks.

FIGS. 12-14 present images of the treated area, demonstrating the effect of the therapy on the condyloma at bi-weekly intervals during the period of treatment. As is shown in, for example, FIGS. 14*a-b*, at the end of the period of treatment, the wart substantially sloughed off, leaving no scar on the treated area.

Example 6

Treatment of Condyloma Acuminatum with a Tellurium Composition

A 25-years old female with condyloma acuminata in the genital region was treated with Composition 1 (described in Example 1 hereinabove) by topically applying the composition twice daily on and around the affected area for a period of about 4 weeks.

FIGS. 15-17 present images of the treated area, demonstrating the effect of the therapy on the condyloma at bi-weekly intervals during the period of treatment. As is shown in, for example, FIG. 17, at the end of the period of treatment, the wart substantially sloughed off, leaving no scar on the treated area.

Example 7

Treatment of Condyloma Acuminatum with a Tellurium Composition

A 28-years old female with condyloma acuminata in the genital region was treated with Composition 1 (described in Example 1 hereinabove) by topically applying the composition twice daily on and around the affected area for a period of about 2 weeks.

FIGS. 18-19 present images of the treated area, before (FIG. 18) and after (FIG. 19) treatment with a composition according to the present invention, demonstrating the effect of the therapy on the condyloma during the period of treatment. As is shown in FIG. 19, at the end of the period of treatment, the wart substantially sloughed off, leaving no scar on the treated area.

Example 8

Treatment of Condyloma Acuminatum with a Tellurium Composition

A 29-years old male with condyloma acuminata in the anus was treated with Composition 1 (described in Example 1 hereinabove) by topically applying the composition twice daily on and around the affected area for a period of about 8-9 weeks.

FIGS. 20-23 present images of the treated area, demonstrating the effect of the therapy on the condyloma after two days (FIG. 21) about 5 weeks (FIG. 22) and about 8 weeks of therapy. As is shown in, for example, FIG. 23, at the end of the period of treatment, the wart substantially sloughed off, leaving no scar on the treated area.

Example 9

Treatment of Verruca Vulgaris with a Tellurium Composition

A 18-years old female with verruca vulgaris on both hands was treated with Composition 2 (described in Example 1 hereinabove) by topically applying the composition twice daily on and around the affected area for a period of about 6-7 weeks.

FIGS. 24-26 present images of the treated area, demonstrating the effect of the therapy on the verruca vulgaris after about 3 weeks (FIGS. 25 *a-b*) and about 6 weeks (FIGS. 26 *a-b*) of treatment.

Example 10

Treatment of Condyloma Acuminata with a Tellurium Composition

A 28-years old female with condyloma acuminata in the genital was treated with Composition 1 (described in Example 1 hereinabove) by topically applying the composition twice daily on and around the affected area for a period of about 8 weeks.

FIGS. 27*a-d* present images of the treated area, which show the effect of the therapy on the condyloma acuminata at about bi-weekly or tri-weekly intervals during the period of treatment.

Example 11

Treatment of Condyloma Acuminata with a Tellurium Composition

A 35-years old female with condyloma acuminata in the genital was treated with Composition 1 (described in Example 1 hereinabove) by topically applying the composition twice daily on and around the affected area for a period of about 8-9 weeks.

FIGS. 28*a-d* present images of the treated area, which show the effect of the therapy on the condyloma acuminata at about bi-weekly or tri-weekly intervals during the period of treatment.

Example 12

Treatment of Condyloma Acuminatum with a Tellurium Composition

A 27-years old male with condyloma acuminata in the anus was treated with Composition 1 (described in Example 1 hereinabove) by topically applying the composition twice daily on and around the affected area for a period of about 10 weeks.

FIGS. 29*a-e* present images of the treated area, demonstrating the effect of the therapy on the condyloma after at about bi-weekly or tri-weekly intervals during the period of treatment.

Example 13

Treatment of Condyloma Acuminatum with a Tellurium Composition

A 25-years old male with condyloma acuminata in the anus was treated with Composition 1 (described in Example 1 hereinabove) by topically applying the composition twice daily on and around the affected area for a period of about 10 weeks.

FIGS. 30a-d present images of the treated area, demonstrating the effect of the therapy on the condyloma after about 4 weeks' intervals during the period of treatment.

Example 14

Treatment of Verruca Vulgaris with a Tellurium Composition

Open Use Pilot Study

Protocol:

Twenty-eight patients (19 men and 9 women) aged 17-72 years (mean 26 years) were enrolled in an open use pilot study. All patients had typical verruca vulgaris of the hands. Eleven of them had relatively new lesions (of less than 6 months) which had not been treated previously, while the other 17 had long-standing, heavily pre-treated (including liquid nitrogen, laser, salicylic acid, etc.) lesions.

Two patients were immunosuppressed (post recent heart and bone marrow transplants). An additional patient had received chemotherapy a few months previously for lung carcinoma (complete remission during the protocol treatment period) and another patient had surgery one month prior to the study for carcinoma of the thyroid.

1. All patients were examined by the protocol physicians, so as to evaluate the ability of AS101 to eradicate verruca vulgaris and the safety of the topical application.

A 10% solution of ammonium trichloro (dioxoethylene-O, O') tellurate (AS-101) in DMSO (Composition 3 in Example 1 hereinabove) was applied on and around a single lesion twice daily, two drops in the morning and two drops at night for three weeks. Patients were examined once a week in the period of treatment and a bi-weekly follow up was carried out for 3-12 weeks post treatment. In patients with multiple warts, only one wart was selected for treatment.

A complete response was defined as the total disappearance of the wart; a major response was over 80% reduction in the size and an overall response in those who had either a complete response or a major response.

Results:

Twenty-three patients were available for evaluation at the end of the study. Five patients stopped treatment for unclear reasons. After three weeks of treatment, a complete response was observed in 10 out of 23 (43%) of the patients and a lesser response in 3 out of 23 (13%). Seven of the patients who had a major response were treated for another three weeks. At the end of the additional three weeks, one patient had a complete response while another showed further improvement.

Overall response (complete or major) was observed in 20 out of 23 patients (87%) after 3-6 weeks of treatment. The response rate was unrelated to the previous treatment and was the same for previously treated and untreated warts.

No side effects were observed besides the temporary (several days duration) black discoloration around the wart, and sometimes sublingually, which was reported by some of the patients in the study. Some patients experienced slight pain for a few hours following the application. This pain was significantly less than the pain caused by the use of liquid nitrogen in the cryosurgical removal of warts.

Example 15

Treatment of Condyloma Acuminata in Females with a Tellurium Composition

Open Use Pilot Study

Protocol:

Female patients aged 18 years and up were enrolled in an open use pilot study. All patients had diagnosed HPV genital warts.

Patients were examined by the protocol physicians, so as to evaluate the ability of AS101 to eradicate Condyloma Acuminata and the safety of the topical application.

A 20% cream composition (Composition 1 described in Example 1 above) was applied on and around the targeted area twice daily, and was maintained for at least two hours before taking a shower. Patients were examined every other week during treatment and every two months for a six months post treatment period.

A complete response was defined as a reduction of 95-100% in the size of the warts (averaged); a partial response was defined as a reduction of 70-94% in the size of the warts (averaged); and no response was defined as less than 70% reduction in the size of the warts (averaged).

Results:

This study is still ongoing, and therefore conclusive data has not been established yet. Preliminary results, however, obtained regarding the 21 patients who completed the treatment indicate a complete cure in 18 patients (85.7%), following a treatment period ranging between a minimum period of 14 days and a maximal period of 84 days (an average treatment period of 38 days), and no response in 1 patient (4.7%). Two patients were dropped out of the trial voluntarily.

Local, light to moderate anticipated side effects such as erythrema, itching, slight burn and the like were observed in 9 of the 21 patients (42.8%), whereby non-local adverse effects such as allergic reaction or strong local burn were observed in 3 patients (14.2%).

Example 16

Treatment of Condyloma Acuminata in Males with a Tellurium Composition

Open Use Pilot Study

Protocol:

Male patients aged 18 years and up were enrolled in an open use pilot study. All patients had diagnosed HPV in the anus.

All patients were examined by the protocol physicians so as to evaluate the ability of AS101 to eradicate Condyloma Acuminata and the safety of the topical application.

A 20% cream composition (Composition 1 described in Example 1 above) was applied on and around the targeted area twice daily. Patients were examined on a bi-weekly basis during treatment and every two months for a six months post treatment period.

A complete response was defined as a reduction of 95-100% in the size of the warts (averaged); a partial response was defined as a reduction of 70-94% in the size of the warts (averaged); and no response was defined as less than 70% reduction in the size of the warts (averaged).

Results:

Since the studies described above are still ongoing, conclusive data has not been established yet. Preliminary results, however, obtained regarding the 12 patients who completed the treatment indicate a complete cure in 7 patients (53.8%), following a treatment period ranging between a minimum period of 42 days and a maximal period of 105 days (an average treatment period of 67 days), and no response in 3 patients (25%). One patient dropped out of the trial voluntarily.

Local, light to moderate anticipated side effects such as erythrema, itching, slight burn and the like were observed in 9 of the 12 patients (75%), whereby non-local adverse effects such as allergic reaction, or strong local burn were observed in 2 patients (16.6%).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a skin or mucosal membrane ailment caused by a human papilloma virus (HPV) in a subject in need thereof, the method comprising administering to the subject a therapeutically effective amount of a tellurium-containing compound having the formula:

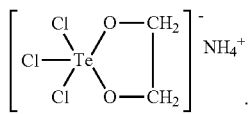

2. The method of claim 1, wherein said administering is effected systemically.

3. The method of claim 2, wherein said therapeutically effective amount ranges from about 0.01 mg/m$^2$/day to about 10.0 mg/m$^2$/day.

4. The method of claim 1, wherein said administering is effected, topically.

5. The method of claim 1, wherein said skin or mucosal membrane ailment is selected from the group consisting of verruca vulgaris, plantar warts, palmar warts, periungal warts, planar warts, mosaic warts, genital warts, venereal warts (condylomata acuminata), butcher's warts, malignant epidermodyspasia verruciformis, advanced intraepithelial dysplasia, cervical cancer, mepidermodysplasia verruciformis, cutaneous warts in immunosuppressed patients, laryngeal papillomas and oral papilloma.

6. The method of claim 1, further comprising administering to the subject an additional active agent.

7. The method of claim 6, wherein said additional active agent is selected from the group consisting of an antibiotic agent, an antimicrobial agent, an anti-acne agent, an antibacterial agent, an antifungal agent, an antiviral agent, a steroidal anti-inflammatory agent, a non-steroidal anti-inflammatory agent, an anesthetic agent, an antipruriginous agent, an antiprotozoal agent, an anti-oxidant, a chemotherapeutic agent, an antidepressant, an anti histamine, a vitamin, a hormone, a keratolytic agent and an antidandruff agent.

8. The method of claim 1, further comprising administering to the subject at least one additional active agent being capable of treating said skin or mucosal membrane ailment caused by HPV.

9. The method of claim 1, wherein said tellurium-containing compound forms a part of a pharmaceutical composition, said pharmaceutical composition further comprising a pharmaceutically acceptable carrier.

10. The method of claim 9, wherein a concentration of said tellurium-containing compound ranges from about 0.01 weight percent to about 50 weight percents of the total weight of said composition.

11. The method of claim 10, wherein a concentration of said tellurium-containing compound ranges from about 5 weight percents to about 25 weight percents of the total weight of said composition.

12. The method of claim 9, wherein said pharmaceutical composition further comprises at least one additional active agent.

13. The method of claim 9, wherein said pharmaceutical composition has a pH that ranges from 4 to 7.

* * * * *